United States Patent [19]
Casasent
[11] Patent Number: 4,906,099
[45] Date of Patent: Mar. 6, 1990

[54] METHODS AND APPARATUS FOR OPTICAL PRODUCT INSPECTION

[75] Inventor: David P. Casasent, Pittsburgh, Pa.
[73] Assignee: Philip Morris Incorporated, New York, N.Y.

[21] Appl. No.: 115,428
[22] Filed: Oct. 30, 1987
[51] Int. Cl.[4] .............................................. G01B 11/00
[52] U.S. Cl. ........................................ 356/394; 382/8; 382/41
[58] Field of Search ...................... 356/394; 382/8, 25, 382/41, 46, 30; 350/433

[56] References Cited

U.S. PATENT DOCUMENTS

| | | | |
|---|---|---|---|
| 988,720 | 4/1911 | Kohler | 350/420 |
| 3,069,654 | 12/1962 | Hough | 340/146.3 |
| 4,242,702 | 12/1980 | Kuni et al. | 358/106 |
| 4,493,554 | 1/1985 | Pryor et al. | 356/394 |
| 4,515,480 | 5/1985 | Miller et al. | 356/394 |
| 4,618,989 | 10/1986 | Tsukune et al. | 382/25 |

FOREIGN PATENT DOCUMENTS

| | | | |
|---|---|---|---|
| 205628 | 12/1986 | European Pat. Off. . | |
| 2704983 | 8/1978 | Fed. Rep. of Germany | 356/394 |
| 61-290583 | 12/1986 | Japan . | |

OTHER PUBLICATIONS

Van Daele et al., "The Leuven Automatic Visual Inspection Machine", *Proceedings of the Society of Photo-Optical Instrumentation Engineers*, vol. 182 (1979) pp. 58–64.
Van Daele et al., "Automatic Visual Inspection of Reed Switches", *Optical Engineering*, vol. 19, No. 2, (Mar.-/Apr. 1980) pp. 240–244.
Wai-Hon Lee, "Computer-Generated Holograms; Techniques and Applications", in *Progress in Optics*, vol. XVI, pp. 121–232, North-Holland Publishing Company, Amsterdam, 1978.
D. Casasent, "Coherent Optical Pattern Recognition", *Proceedings of the IEEE*, vol. 67, No. 5, May 1979, pp. 813–825.
G. R. Gindi et al., "Optical Feature Extraction Via the Radon Transform", *Optical Engineering*, vol. 23, No. 5, Sep./Oct. 1984, pp. 499–506.
D. Casasent, "Computer Generated Holograms in Pattern Recongition: A Review", *Optical Engineering*, vol. 24, No. 5, Sep./Oct. 1985, pp. 724–730.
W. H. Steier et al., "Optical Hough Transform", *Applied Optics*, vol. 25, No. 16, Aug. 1986, pp. 2734–2738.
C. Barney, "Hologram Filter Spots Images from Any Angle", *Electronics*, Sep. 4, 1986, pp. 37–38.
R. Krishnapuram, "Hough Space Transformations for Discrimination and Distortion Estimation", *Computer Vision, Graphics, and Image Processing*, vol. 38, No. 3, Jun. 1987, pp. 299–316.

*Primary Examiner*—Richard A. Rosenberger
*Attorney, Agent, or Firm*—Robert R. Jackson

[57] ABSTRACT

Products having optically detectable straight line segments are inspected for acceptability by forming one or more one-dimensional images of the product in which properly aligned straight line segments are respectively focused to points in the image. Such parameters as the location and image intensity of these one-dimensional image points are used to determine whether or not the product is acceptable. An optical Hough transform underlies these product inspection techniques.

34 Claims, 18 Drawing Sheets

METHODS AND APPARATUS FOR OPTICAL PRODUCT INSPECTION

BACKGROUND OF THE INVENTION

This invention relates to methods and apparatus for optically inspecting products, and more particularly to methods and apparatus for determining whether or not a product has predetermined optically detectable characteristics.

Certain high-volume, mass-produced consumer products are made in such large quantities and at such high speeds that conventional inspection methods are either impractical or impossible. Nevertheless, it is important to ensure that the products are satisfactory in appearance, quality, etc. For example, cigarette packages may come off a cigarette-making machine at the rate of 360 per minute, and cigarette manufacturers are attempting to achieve substantially greater speeds (e.g., 750 packages per minute or more). At these speeds, it is extremely difficult, using conventional inspection techniques, to make sure that the packaging for each pack has been properly folded around the cigarettes, that the printing on the packaging is properly aligned and centered, that the tax stamp has been applied and is properly centered and aligned, that the tear strip is present and properly located, etc. Similar inspection problems occur in the production of many other products such as packaged foods and beverages, toilet articles and medicines, soaps and detergents, paper products, magazines, books, etc.

Illustrative of the shortcomings of conventional inspection methods and apparatus are the difficulties encountered in attempting to use the conventional electro-optical technique of having multiple photocells monitor the optical properties of the product at a multiplicity of points on the surface of the product. Among the difficulties with this technique at high product speeds is the fact that it may be extremely costly or even impossible to process the resulting data sufficiently rapidly to keep up with the product stream. Another problem with this technique is that it is typically very sensitive to slight variations in product location or orientation on the apparatus which is conveying the product through the inspection station. In other words, the product may be erroneously identified as not having the predetermined optical characteristics simply because of variability in the conveyor apparatus. Conventional systems employing a camera or similar two-dimensional detector array sensor to provide an image of the object have similar deficiencies.

In view of the foregoing, it is an object of this invention to provide improved product inspection methods and apparatus.

It is a more particular object of this invention to improve the speed, performance, and flexibility of product inspection methods and apparatus by performing more of the necessary information processing optically.

SUMMARY OF THE INVENTION

These and other objects of this invention are accomplished in accordance with the principles of the invention by providing methods and apparatus for determining whether or not a product has at least one optically detectable straight line segment having a predetermined orientation in a predetermined object plane. In accordance with the invention, a one-dimensional image of the object plane is formed by integrating a two-dimensional image of the object plane parallel to the predetermined orientation so that each straight line segment having the predetermined orientation in the object plane is focused to a point in the one-dimensional image. The image intensity of the point in the one-dimensional image is proportional to such parameters as the length and image intensity of the line segment. The one-dimensional image is monitored to determine whether or not it includes a point having the image intensity that would result if the object plane included the desired straight line segment at the predetermined orientation. The product is then indicated to have the predetermined optical characteristics depending on whether or not the one-dimensional image is found to include a point having the foregoing image intensity. If desired, additional optical characteristic criteria (e.g., line location) can be included by requiring the resulting point in the one-dimensional image to be at a particular location in that image. If the product has two or more optically detectable, parallel, straight line segments, the spacing between the resulting points in the one-dimensional image can also be used to determine whether or not the product has the appropriately spaced, parallel, straight line segments.

Further features of the invention, its nature and various advantages will be more apparent from the accompanying drawings and the following detailed description of the invention.

DETAILED DESCRIPTION OF THE INVENTION

There are many reasons why it may be desired to inspect products in accordance with this invention. For example, it may be desired to determine whether or not a product meets certain visual acceptance criteria. Or it may be desired to identify two or more different products, or products having different orientations at the inspection location. Once identified as having or not having the predetermined optically detectable characteristics, it may be desired to further process the product differently depending on whether or not it has those characteristics. For example, if product acceptability is being determined, it may be desired to deface or label an unacceptable product, and/or to separate that product from other products found to be acceptable. Similarly, different further processing may be desired for products identified as being of different types, as having different orientations, etc. Because determining product acceptability is representative of many of the possible applications of this invention, many of the embodiments of the invention will be described herein in that context. It is to be understood, however, that determining product acceptability is merely illustrative of the possible uses of the invention, and that the invention is not limited to making product acceptability determinations. Similarly, although the invention is applicable to inspecting many other types of products, the invention will be fully understood from an explanation of its application to inspecting cigarette packages.

Figure 1:
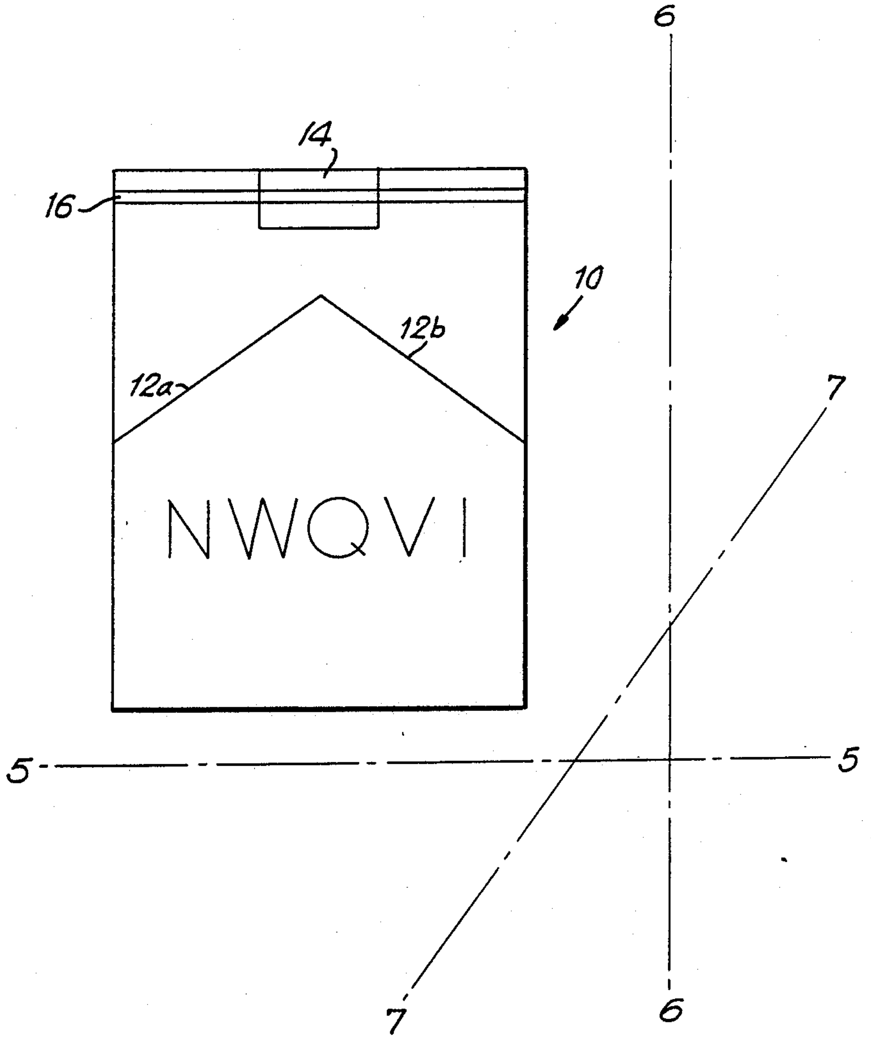
FIG. 1 is simplified elevational view of a typical product to be inspected in accordance with the principles of this invention.

The front of an illustrative cigarette package 10 (with all text—except for a few arbitrary product name letters—deleted) is shown in FIG. 1. Package 10 includes some printed ornamentation (e.g., lines 12*a* and 12*b*), a tax stamp 14 partly visible in FIG. 1 and additionally extending over the top of the package, and a tear strip 16 for assisting the consumer in removing the transparent outer cellophane wrapper.

Although FIG. 1 shows a perfect (and therefore acceptable) cigarette package, many types of defects can occur to render the package unacceptable. For example, the package could be folded improperly so that the printing (including the letters NWQVI and ornamentation lines 12) might not have the proper position or orientation. Tax stamp 14 could be missing entirely, or if present, could be skewed or off-center (e.g., to the left or right, up or down as viewed in FIG. 1). Tear strip 16 could also be missing or mislocated.

Testing for all of these (and many other) possible defects using conventional technology becomes increasingly difficult as product manufacturing speeds increase.

Figure 2:
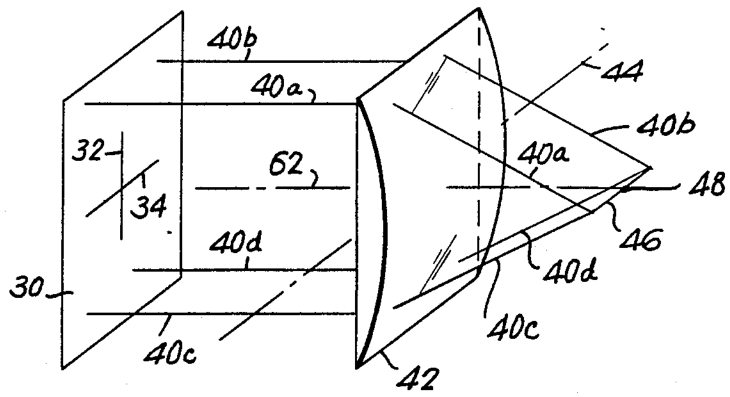
FIG. 2 is a perspective view of apparatus which can be used to form a one-dimensional image of a two-dimensional object.

FIG. 2 shows one illustrative embodiment of one component part of this invention which addresses this problem. In FIG. 2, element 30 is a two-dimensional object plane (such as the front of cigarette package 10 or a two-dimensional image of the front of cigarette package 10). For purposes of illustration, object plane 30 is assumed to include (in addition to its peripheral edges) two optically detectable straight line segments 32 and 34. Straight line segment 32 is vertical, while straight line segment 34 is horizontal.

Collimated light from object plane 30 (indicated by representative light rays 40*a–d*) is applied to conventional cylindrical lens 42 (e.g., a lens which is planar on the side facing object plane 30 and semi-cylindrical on the other side). Cylindrical lens 42 has a longitudinal axis 44 which is horizontal. Accordingly, cylindrical lens 42 focuses all of the light from object plane 30 into a single horizontal line 46 which is therefore a particular one-dimensional image of the object plane.

Note that in FIG. 2 the longitudinal axis 44 of cylindrical lens 42 is parallel to horizontal line 34, and therefore perpendicular to vertical line 32. As a result, the longitudinal axis of one-dimensional image 46 is also parallel to horizontal line 34 and perpendicular to vertical line 32. This in turn means that the optical energy or information associated with or attributable to horizontal line 34 is distributed along image 46, whereas the optical energy or information associated with or attributable to vertical line 32 is all concentrated at a single point 48 in image 46. (As used herein and in the appended claims, the word "point" is used to mean a small area within which further dimensional analysis is not needed and is therefore irrelevant. Thus the word point is used herein in somewhat the way that it is used in mathematics, except that (because physical as opposed to purely mathematical phenomena are involved) a point herein has a small but finite area.)

Figure 3:
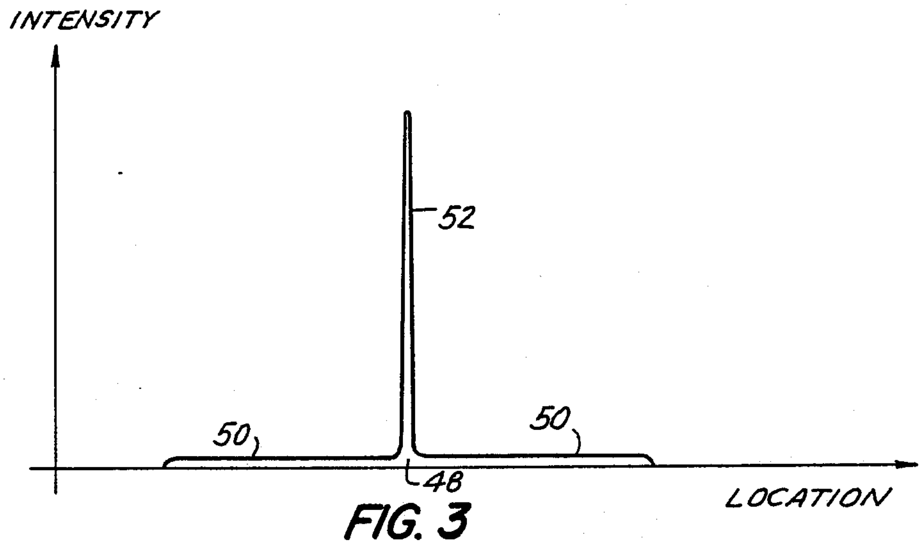
FIG. 3 is a plot of image intensity for a particular one-dimensional image formed by the apparatus of FIG. 2.

Assuming that nothing other than lines 32 and 34 contributed to the intensity of image 46, a plot of the intensity of image 46 would be as shown in FIG. 3. The relatively low amplitude portion 50 of the curve in FIG. 3 is due to horizontal line segment 34. The highly concentrated, high-amplitude spike 52 is due to vertical line segment 32. The location of spike 52 is determined by the left-right location of vertical line segment 32. (Note that the vertical location of line segment 32 is irrelevant.) The height of spike 52 is a function of (1) the length of line segment 32 and (2) the optical intensity of line segment 32.

Figure 4A:
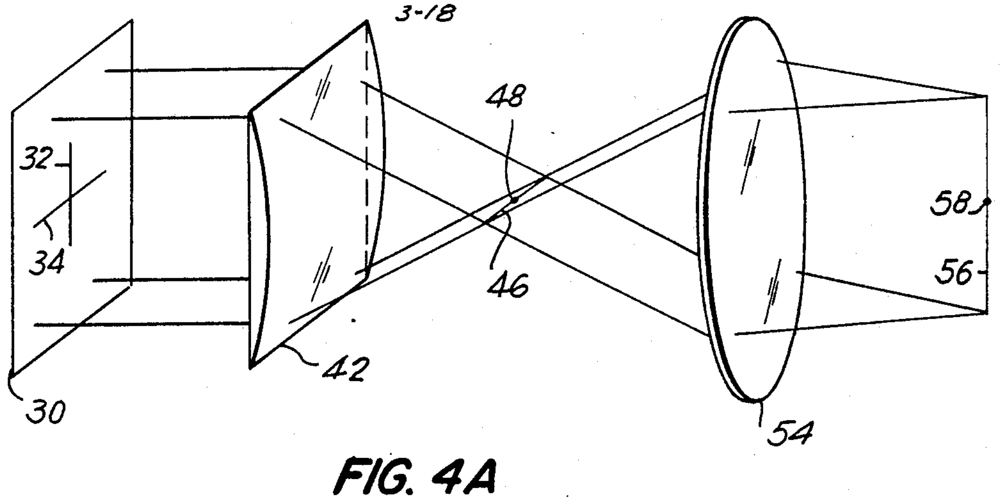
FIG. 4A is a perspective view of alternative apparatus for forming one-dimensional images of a two-dimensional object.

In FIG. 4A a conventional spherical lens 54 has been added to the right of one-dimensional image 46. The effect of spherical lens 54 is to cause formation of a second one-dimensional image 56 of two-dimensional object plane 30. The longitudinal axis of one-dimensional image 56 is perpendicular to the longitudinal axis of one-dimensional image 46. In image 56 the effect of vertical line segment 32 is dispersed, while the effect of horizontal line segment 34 is concentrated at a single point 58. Thus a plot of the intensity of image 56 would be similar to FIG. 3, except that the low-amplitude portion 50 would be due to vertical line segment 32, and the spike 52 would be due to horizontal line segment 34.

Figure 4B:
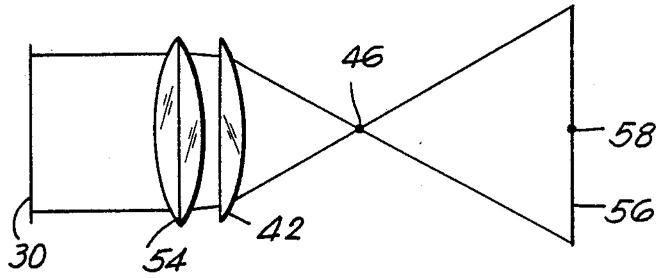
FIG. 4B is a side view of another alternative apparatus for forming one-dimensional images of a two-dimensional object.

Another way to form two orthogonal one-dimensional images of object plane 30 is to reverse the order of lenses 42 and 54, and place them closer together, as shown in FIG. 4B. This causes both one-dimensional images to form to the right of the right-most lens. As compared to FIG. 4A in which both one-dimensional images can be readily made to have the same size, the alternative of FIG. 4B tends to produce one-dimensional images of different sizes (i.e., it reduces the size of horizontal one-dimensional image 46 which forms closest to cylindrical lens 42, and increases the size of vertical one-dimensional image 56 which forms farther from the cylindrical lens). This may be undesirable if both one-dimensional images are to be used, because it means that different size detectors must be used for each one-dimensional image. On the other hand, the alternative of FIG. 4B has been found to produce better one-dimensional images with low-cost lenses than the arrangement shown in FIG. 4A. The alternative of FIG. 4B can also be made shorter than FIG. 4A, which may make it easier and cheaper to manufacture.

Although FIGS. 2, 4A, and 4B show some of the possible lens systems which can be used to form one-dimensional images, those skilled in the art will appreciate that there are many other lens systems (e.g., combinations of two or three cylindrical lenses) which can be used for this purpose.

Figure 4C:
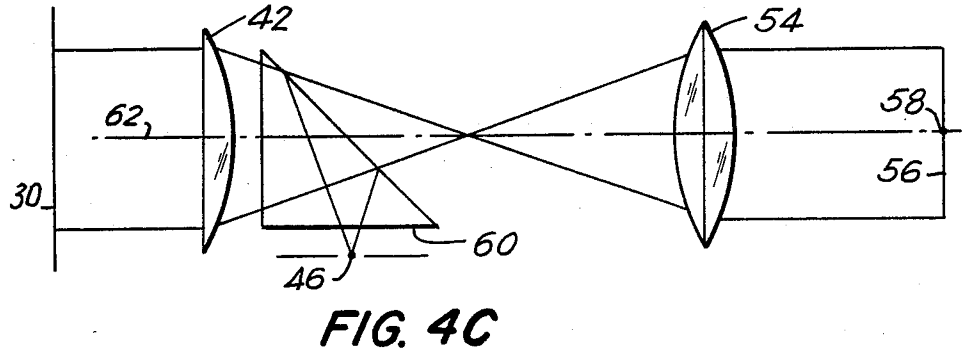
FIG. 4C is a side view showing a possible modification of the apparatus of FIG. 4A.

FIG. 4C shows how a beam splitter 60 can be included between lenses 42 and 54 in the embodiment of FIG. 4A so that a detector can be located to detect horizontal one-dimensional image 46 without interfering with the formation and detection of vertical one-dimensional image 56. Part of the light from lens 42 is reflected off the inclined surface of beam splitter 60 to cause formation of horizontal one-dimensional image 46 at a location off the optical axis 62 of the lens system. The remainder of the light from lens 42 continues on to spherical lens 54 which forms vertical one-dimensional image 56 as described above. A similar beam splitting arrangement could be used in FIG. 4B (e.g., by placing the beam splitter 60 between cylindrical lens 42 and the depicted location of horizontal one-dimensional image 46).

Although in subsequent portions of this disclosure various techniques for forming one-dimensional images having any orientation are discussed, apparatus of the type shown in FIGS. 2 and 4C is useful in many product inspection applications because in many such applications, a product can be adequately inspected from just one angle using apparatus of the type shown in FIG. 2, or from just two orthogonal angles (e.g., parallel to the horizontal and vertical edges of the product) using apparatus of the type shown in FIG. 4C.

Returning to FIG. 2, if vertical line segment 32 were even slightly rotated (i.e., no longer exactly perpendicular to axis 44), spike 52 in FIG. 3 would be shorter and wider. The height and width of spike 52 can therefore be used to determine whether or not line segment 32 is properly aligned perpendicular to the longitudinal axis of one-dimensional image 46. If spike 52 is found not to be sufficiently high and/or sufficiently narrow, the product associated with object plane 30 can be rejected as unsatisfactory.

As suggested above, the height of spike 52 is also directly proportional to the length of line segment 32 and to the optical intensity of that line segment. Thus even if spike 52 has the desired narrowness, if spike 52 is too high or too low, the product associated with object plane 30 can be rejected as unsatisfactory. For example, spike 52 might be too high because line segment 32 was smeared in the vertical direction. Or spike 52 might be too low because line segment 32 was broken or not printed with sufficient intensity.

As also suggested above, the left-right location of line segment 32 determines the left-right location of spike 52. Thus yet another test for product acceptability can be based on the left-right location of spike 52. If spike 52 is not found at the desired location, then either line segment 32 is not present at all, or it has been shifted to the left or right. In either case, the product associated with object plane 30 can be rejected on that basis.

If the product associated with object plane 30 were travelling on a conveyor system parallel to line segment 34, the above-described shifting of spike 52 might be due to improper positioning of the product on the conveyor, rather than to a defect in the product. However, if an acceptable product has two or more parallel vertical lines (such as a left or right edge and a vertical line at a predetermined desired horizontal distance from that edge), then the spacing between the peaks in one-dimensional image 46 (rather than the absolute locations of the peaks) can be used to determine product acceptability independent of possible translations of the product parallel to object plane 30.

Figure 5:
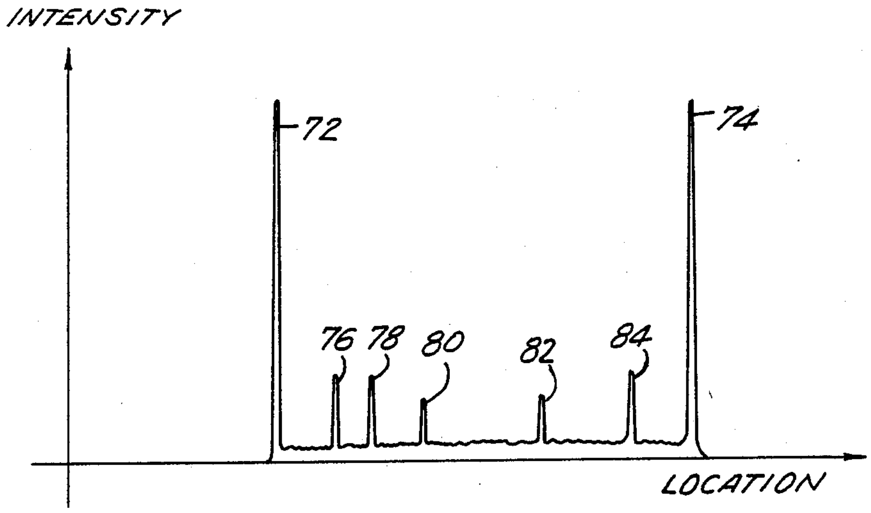
FIG. 5 is a plot of image intensity for a particular one-dimensional image of the product of FIG. 1.

The object plane pattern depicted in FIG. 2 is, of course, extremely simple. FIG. 5 shows the one-dimensional image 46 that results from substituting the pattern of FIG. 1 in the apparatus of FIG. 2. Initially it is assumed that the vertical side edges of the package of FIG. 1 are vertical in FIG. 2 (i.e., the one-dimensional image of FIG. 5 is parallel to axis 5—5 in FIG. 1). Spikes 72 and 74 are respectively produced by the left- and right-hand vertical edges of package 10. These spikes are very high because the vertical edges of the package are relatively long. Spikes 76 and 78 are respectively produced by the left- and right-hand vertical portions of the letter N printed on the front package 10. Spikes 80 and 82 are respectively produced by the left- and right-hand edges of tax stamp 14. Spike 84 is produced by the vertical portion of the printed letter I. The remainder of the image intensity plotted in FIG. 5 has relatively low amplitude because there are no other vertical line segments to cause prominent peaks to form in it.

Many tests of product acceptability can be performed on the data plotted in FIG. 5. For example, the characteristics of peaks 76, 78, and/or 84 can be used to determine such factors as: (1) whether or not the lettering is printed with sufficient intensity (these peaks will tend to be too short if the printing is not sufficiently intense); (2) whether or not the lettering is smeared in the vertical direction (these peaks will tend to be too high if the printing is smeared vertically); (3) whether or not the printing is shifted left or right (these peaks will be correspondingly shifted left or right); (4) whether or not the printing is improperly tilted (these peaks will tend to be shorter and broader if the printing is tilted either way); (5) whether or not the printing is smeared horizontally (these peaks will tend to be broader if the printing is smeared horizontally); and (6) whether or not the printing is present (these peaks will be absent if the printing is absent). Similarly, the characteristics of peaks 80 and/or 82 can be used to determine such factors as: (1) whether or not tax stamp 14 is present (these peaks will be missing if tax stamp 14 is absent); (2) whether or not tax stamp 14 is shifted left or right (these peaks will be correspondingly shifted left or right); (3) whether or not the appropriate amount of tax stamp 14 is showing on the front of package 10 (these peaks will be too high if too much of tax stamp 14 is visible, and too low if too little of tax stamp 14 is visible); (4) whether or not a corner of tax stamp 14 has been folded up or under (these peaks will not be of equal height if one corner of tax stamp 14 has been folded up or under); and (5) whether or not tax stamp 14 is crooked on the package (these peaks will be shorter and broader if the tax stamp is crooked). In addition to the foregoing, the presence of other unintended peaks or amplitude values may indicate other defects in package 10. For example, another peak may indicate a smudge or smear on the package which should cause the package to be rejected as defective.

Further data about the acceptability of package 10 can be gathered by forming one-dimensional images having other orientations. For example, one-dimensional image 56 (FIG. 4A) is perpendicular to image 46 and is therefore parallel to axis 6—6 in FIG. 1. Another way to form a one-dimensional image having this orientation is to rotate object plane 30 or cylindrical lens 42 by 90° about axis 62 in FIG. 2. A plot of the intensity of the resulting one-dimensional image is shown in FIG. 6.

Figure 6:
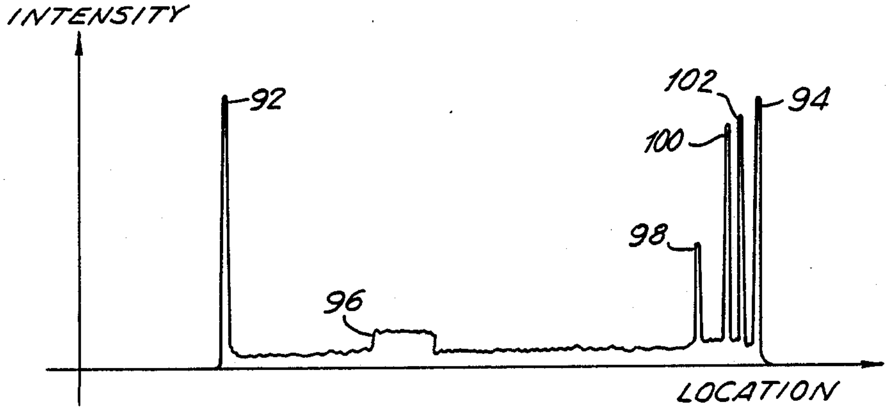
FIGS. 6 and 7 are similar to FIG. 5 but for other one-dimensional images of the product of FIG. 1.

In FIG. 6, peaks 92 and 94 are respectively produced by the bottom and top edges of package 10. Region 96 of slightly elevated amplitude is produced by printed letters NWQVI. Peak 98 is produced by the lower edge of tax stamp 14. Peaks 100 and 102 are respectively produced by the lower and upper edges of tear strip 16.

As in the case of FIG. 5, a great many tests of product acceptability can be performed on the data depicted in FIG. 6. For example, the characteristics of peak 98 can be used to determine such factors as: (1) whether or not tax stamp 14 is present (peak 98 will be absent if tax stamp 14 is absent); (2) whether or not tax stamp 14 is crooked (peak 98 will be shorter and broader if tax stamp 98 is rotated either way); and (3) whether the proper amount of tax stamp 14 is showing on the front of package 10 (peak 98 will be shifted left or right if tax stamp 14 is shifted down or up). Similarly, the characteristics of peaks 100 and 102 can be used to determine such factors as: (1) whether or not tear strip 16 is present (peaks 100 and 102 will be absent if tear strip 16 is absent); (2) whether or not tear strip 16 is crooked (peaks 100 and 102 will be shorter and broader if tear strip 16 is inclined in either direction rather than truly horizontal); and (3) whether or not tear strip 16 is properly located (peaks 100 and 102 will be shifted left or right if tear strip 16 is shifted down or up). The left-right location of elevated amplitude portion 96 can be used to determine whether or not letters NWQVI are at the proper vertical location on package 10.

Figure 7:
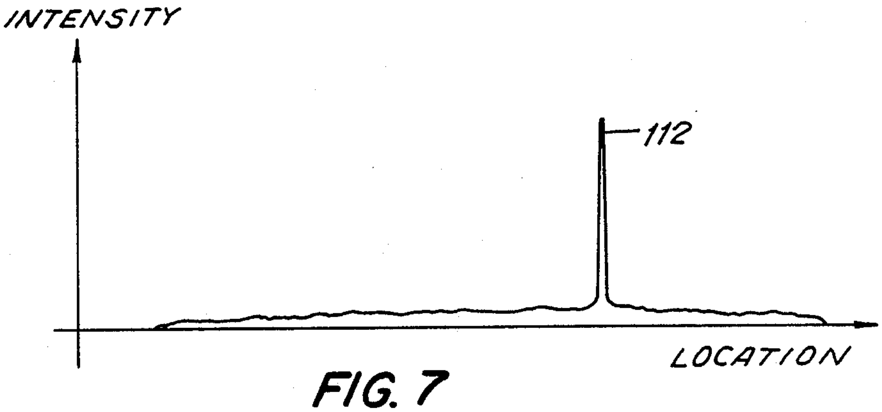

Another useful orientation for a one-dimensional image of package 10 is parallel to axis 7—7 in FIG. 1. This axis is perpendicular to ornamentation line 12b. Such an image can be formed by rotating image plane 30 or cylindrical lens 42 about axis 62 until axis 44 is parallel to axis 7—7. A plot of the image intensity of the resulting one-dimensional image is shown in FIG. 7. Spike 112 is due to ornamentation line 12b. No other prominent peak appears in FIG. 7 because ornamentation line 12b is the only significant straight line segment perpendicular to axis 7—7. Accordingly, the presence or absence of spike 112 indicates the presence or absence of line 12b. Assuming that spike 112 is present, its height and width indicate whether or not line 12b is truly perpendicular to axis 7—7, and its height further indicates the intensity of line 12b, whether or not line 12b is broken or smeared longitudinally, etc.

Among the most useful features of many products for purposes of optical inspection are the edges of the product. This is illustrated by FIGS. 5 and 6 in which peaks 72 and 74 are due to the vertical edges of the product, and peaks 92 and 94 are due to the horizontal edges of the product. Because product edges are frequently so important, it may be desirable to edge-enhance the input image. There are many well-known ways to achieve such edge-enhancement optically (e.g., by spatial filtering, computer generated holograms, spatial light modulators, etc.). Suitably enhanced, edges can often be made the most prominent features in the one-dimensional image. This fact can be used in several ways during the subsequent analysis of the one-dimensional image (e.g., by facilitating alignment of the one-dimensional image with a corresponding reference image). Of course, not all potentially useful one-dimensional images include multiple peaks due to product edges (see, for example, FIG. 7).

Figure 8:
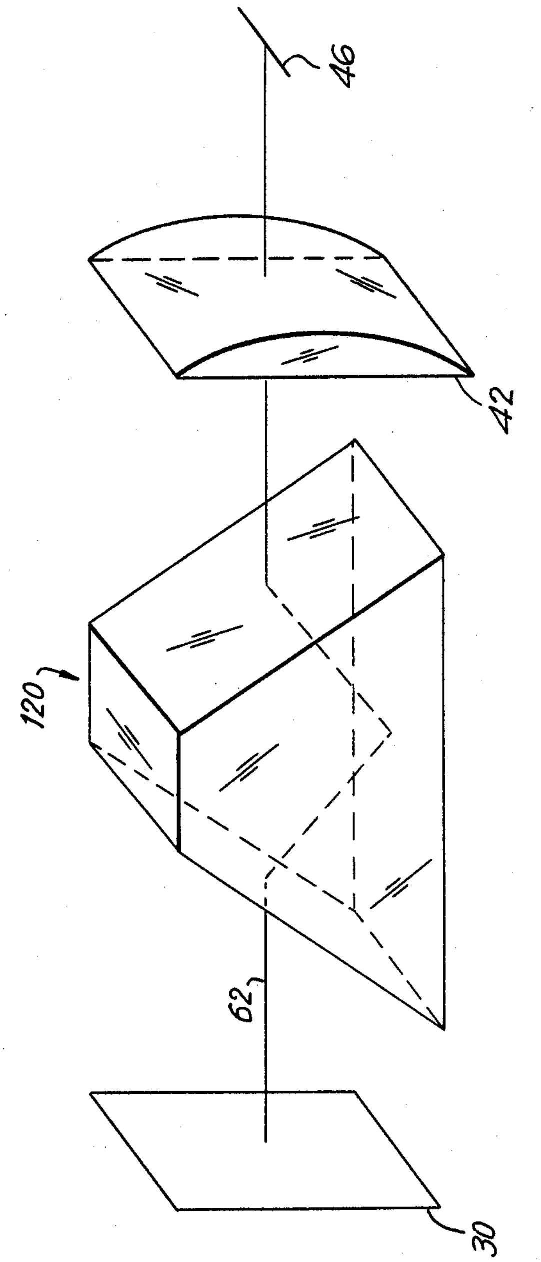
FIG. 8 is a perspective view of still other alternative apparatus for forming one-dimensional images of two-dimensional objects.

As mentioned above, one way to change the orientation of one-dimensional images such as image 46 in FIG. 2 is to rotate image plane 30 or cylindrical lens 42 about axis 62. Another way to accomplish this is to include a rotatable, conventional Dove prism 120 between object plane 30 and cylindrical lens 42 as shown in FIG. 8. (If desired, a spherical lens like spherical lens 54 in FIG. 4B can be included between Dove prism 120 and cylindrical lens 42 in FIG. 8.) The image applied to the left-hand inclined face of Dove prism 120 is refracted down to the bottom surface of the prism. From there it is reflected up to the right-hand inclined face and refracted out again to continue along axis 62. (Note that the effect of Dove prism 120 in the position shown in FIG. 8 is to invert the image from top to bottom but not from left to right.) If Dove prism 120 is now rotated by an angle $\theta$ about axis 62, the output image of the prism rotates by an angle $2\theta$. One-dimensional image 46 stays in the same physical location because lens 42 has not moved, but the effect on the information contained in image 46 is the same as the effect of rotating cylindrical lens 42 about axis 62 by an angle $2\theta$. In other words, rotation of Dove prism 120 allows formation of a one-dimensional image of object plane 30 parallel to any axis of object plane 30. All of these images are focused along the same line 46 because lens 42 does not move. This greatly simplifies detecting the one-dimensional image intensity information at various orientations because the detectors can be stationary (e.g., at the location of line 46).

Although a Dove prism is employed in the illustrative embodiment shown in FIG. 8, those skilled in the art will appreciate that there are other optical devices or systems which can be used to produce the same results.

Figure 9:
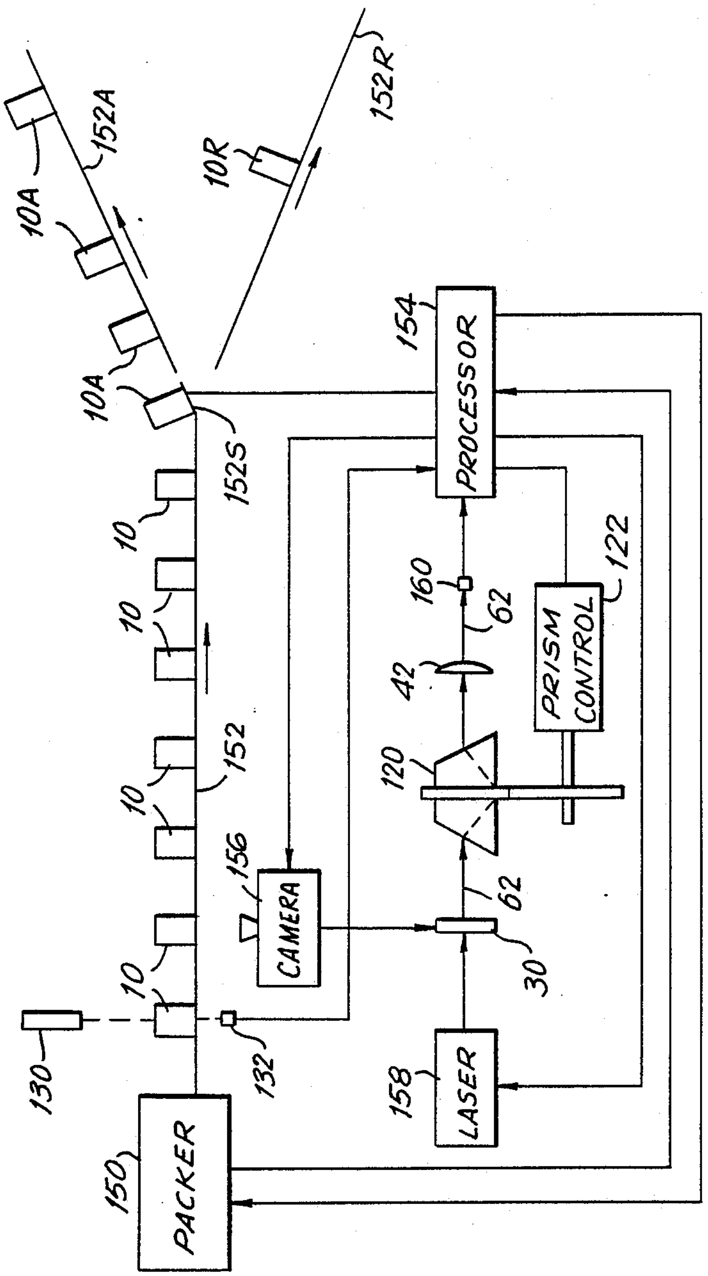
FIG. 9 is a simplified schematic block diagram of illustrative apparatus constructed in accordance with this invention for inspecting products, and for separating products found to be unacceptable from those found to be acceptable.

FIG. 9 shows illustrative product inspection apparatus constructed in accordance with the principles of this invention. Packer 150 (which may be conventional or largely conventional) produces product 10 (e.g., the cigarette packages shown in FIG. 1) which are conveyed one after another from packer 150 by conveyor 152. In order to keep the system synchronized, packer 150 is either controlled by processor 154, or packer 150 produces a periodic signal monitored by processor 154. Alternatively or in addition, a light source 130 and photodetector 132 (or other conventional product detection apparatus) can be used to produce signals applied to processor 154 to keep the optical system synchronized with the movement of products 10 along conveyor 152.

Each time a product 10 reaches the point on conveyor 152 opposite video camera 156, processor 154 causes camera 156 to take a picture of the surface of the product to be inspected. Camera 156 may be a conventional television or charge coupled device ("CCD") camera. Conventional stroboscopic product illumination techniques (not shown but well-known to those skilled in the art) may be used to help camera 156 effectively "freeze" the image of each product 10 even though the products are moving continuously along conveyor 152. A CCD camera is preferable if stroboscopic illumination of product 10 is employed. The image seen by camera 156 is displayed by conventional display 30 (e.g., a liquid crystal display ("LCD") type video screen). Preferably, camera 156 and/or display 30 include conventional means for allowing display 30 to produce a sustained, substantially continuous, fixed image of each product 10 until elements 156 and/or 30 are reset by processor 154 (e.g., when another product is to be imaged by camera 156).

At the same time that the foregoing events are taking place, processor 154 causes prism control 122 to rotate Dove prism 120 about axis 62 to the position required to produce at the location of detector 160 a one-dimensional image of the two-dimensional image on display 30 having a first desired angular orientation. (This assumes, of course, that Dove prism 120 is not already properly oriented, and that one-dimensional images having various angular orientations are desired.) Prism control 122 may be a conventional servo-type motor arranged to rotate Dove prism 120 by any suitable mechanism such as spur gears, timing chains or belts, etc.

Figure 10:
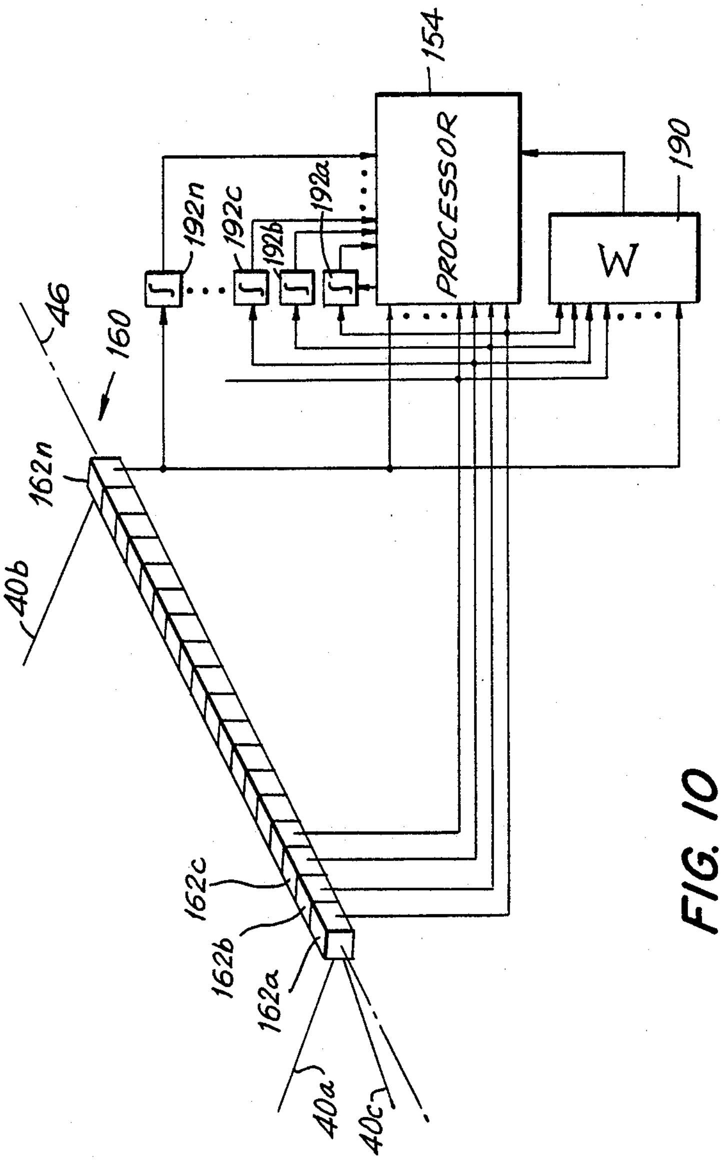
FIG. 10 is a more detailed schematic block diagram showing how a portion of the apparatus of FIG. 9 may be constructed.

As soon as Dove prism 120 is properly positioned, processor 154 causes laser 158 (or any other preferably collimated light source) to briefly illuminate that image. This projects the two-dimensional image on display 30 through Dove prism 120 and cylindrical lens 42 to produce a one-dimensional image having a longitudinal axis perpendicular to the plane of the paper in FIG. 9 at the location of detector 160. (Alternatively, laser 158 can be on continuously and detector 160 switched on at the proper time.) Although other types of detectors 160 may be employed, in the illustrative embodiment shown in FIG. 9, detector 160 comprises (as shown in FIG. 10) a plurality of photo-electric detectors 162*a*–*n* arranged side-by-side along the longitudinal axis 46 of the one-dimensional image. Each photodetector 162 receives a small longitudinal segment of the one-dimensional image and produces an electrical output signal proportional to the amount of light contained in that segment. The output signals of all of photodetectors 162 are applied to processor 154 for processing (as described in more detail below) to determine whether or not the one-dimensional image has the characteristics that would result if the product 10 being inspected were an acceptable product. On that basis, processor 154 records whether or not the product 10 being inspected is acceptable. (Summation device 190 and integrators 192 are not used in this embodiment.) Although FIG. 10 shows parallel read-out of photodetectors 162, the read-out could be serial if desired.

As soon as Dove prism 120 is no longer needed at the first position to form the first one-dimensional image of product 10, processor 154 causes prism control 122 to rotate the Dove prism to the angular position required to produce the second desired one-dimensional image of product 10. (The product image is still on display 30.) For example, assuming that the first one-dimensional image had an optical orientation parallel to axis 5—5 in FIG. 1, that the second one-dimensional image was to have an optical orientation parallel to axis 7—7 in FIG. 1, and that the angle between axes 5—5 and 7—7 is 60°, the desired second one-dimensional image can be produced at detector 160 by an appropriately directed 30° rotation of Dove prism 120 about axis 62.

When prism 120 has been rotated to the position required to produce the second one-dimensional image, processor 154 causes laser 158 to again briefly illuminate the image on display 30. This again projects the two-dimensional product image through elements 120 and 42 to produce the second one-dimensional image at detector 160. Once again, detector 160 produces electrical output signals proportional to the image intensity at each individual photodetector 162. These signals are processed by processor 154 to determine whether or not the second one-dimensional image has the characteristics of the corresponding image for an acceptable product. Again, processor 154 records whether or not the product being inspected is acceptable on that basis.

If yet another one-dimensional image of product 10 is required (e.g., a third image having an optical orientation parallel to axis 6—6 in FIG. 1), then as soon as prism 120 is no longer needed in connection with forming the second image, the prism is rotated a further 15°. As soon as prism 120 is again properly positioned, laser 158 again momentarily illuminates the image on screen 30 to produce the third one-dimensional image at detector 160. The resulting detector 160 output signals are again processed by processor 154 to determine whether or not the third one-dimensional image acceptably agrees with the corresponding image for an acceptable product. Processor 154 again records the results of this test of the acceptability of product 10.

Assuming that the foregoing three one-dimensional images of product 10 are all that are to be tested, after the third one-dimensional image has been detected by detector 160, processor 154 readies the remainder of the apparatus to inspect the next product 10 when it is opposite camera 156 on conveyor 152.

Figure 11:
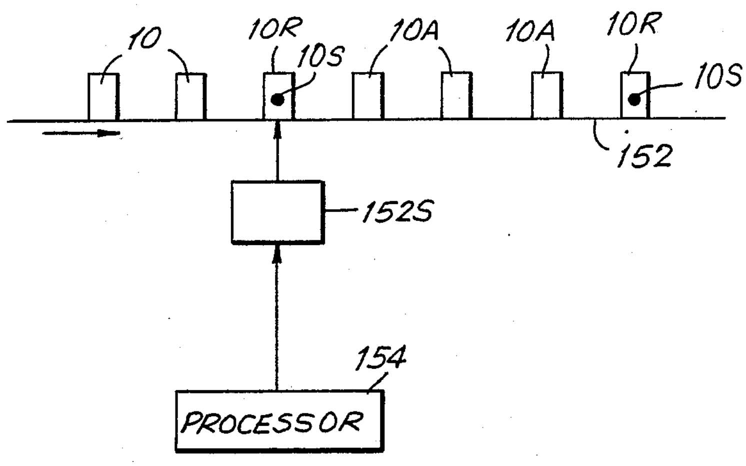
FIG. 11 is a simplified schematic block diagram showing an alternative embodiment of a portion of the apparatus of FIG. 9.

When the product 10 which has just been inspected as described above reaches conveyor portion 152S (for switch), processor 154 controls the position of that portion of the conveyor so that product 10 is directed either to conveyor portion 152A (for accepted) if processor 154 found that all three one-dimensional images of product 10 were sufficiently as expected, or to conveyor portion 152R (for rejected) if processor 154 found that any one or more of those one-dimensional images was deficient in any respect. Products which have been found to be acceptable are identified in FIG. 9 as 10A; products which have been found unacceptable, and which have therefore been rejected, are identified in FIG. 9 as 10R. Conveyor portion 152S, which directs accepted products 10A in one direction and rejected products 10R in another direction, may be any type of controllable product diverter such as a switch in the conveyor mechanism, a mechanical finger selectively interposable in the conveyor path, a controllable air blast for blowing rejected products 10R off the main conveyor path, etc. Alternatively, as shown in FIG. 11, element 152S may not physically separate accepted products 10A from rejected products 10R, but may instead merely mark or otherwise identify or indicate which products are acceptable and which are not. For example, in FIG. 11 device 152S sprays a spot 10S of ink or paint on unacceptable products 10R in order to make possible subsequent identification and/or separation of accepted and rejected products (e.g., by human or robotic product handlers). If desired, processor 154 can feed back signals for controlling packer 150 when unacceptable products are detected. For example, processor 154 could stop packer 150 when unacceptable products are detected. Alternatively, processor 154 could produce signals for causing appropriate adjustment of packer 150 (e.g., to cause a new roll of tax stamps or tear tape to be started if the tax stamp or tear tape is found to be missing from several successive products, to change the intensity of printing if printed features are found to be too light or too dark, etc.).

Figure 12:
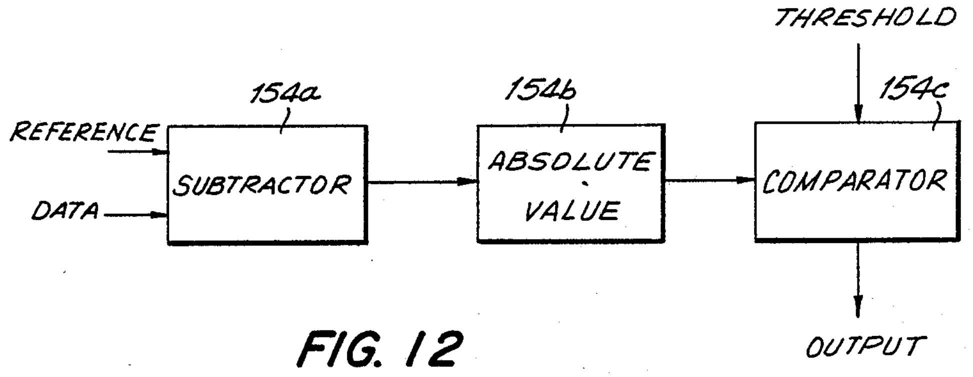
FIG. 12 is a block diagram showing how a portion of the apparatus of FIGS. 9-11 (and other subsequent FIGS.) may operate to analyze one-dimensional image data.

There are several ways in which processor 154 can process the output of detector 160 to determine product acceptability. For example, the value of each photodetector 162 output signal for each one-dimensional image of an acceptable product could be stored in processor 154 as reference image data. Then as the data for each one-dimensional image is received from detector 160, processor 154 subtracts all or selected portions of the appropriate reference image data from the corresponding received data. If the absolute value of any of the resulting differences exceeds a predetermined threshold value, the product can be rejected as unacceptable. The foregoing is illustrated in FIG. 12 in which the stored reference image date ("REFERENCE") and the data from detector 160 ("DATA") are subtracted from one another in subtractor **154*a*, the absolute value of the difference is determined in absolute valuator 154*b*, and the resulting absolute value is compared to a predetermined threshold value in comparator 154*c*. If any threshold value is exceeded, comparator 154*c* produces an output signal indicative that the product is not acceptable. If desired, different threshold values (previously stored in processor 154**) can be used for each point of comparison so that different tolerance levels can be established for each comparison.

If there is a possibility that the product may be shifted left or right relative to camera 10, the resulting data can be effectively shifted to correct for such product shifts before the above-described subtraction is performed. For example, if an edge of the product always produces a large peak, the data can be shifted until that peak is correlated or aligned with the corresponding large peak in the reference image data, and then the reference data can be subtracted from the received data and further processed as described above. Alternatively, the entire detector output data stream can be correlated with the reference image data to determine the best overall match between the detector output and the reference data. For example, in FIG. 13 the reference data is stored in register **154*d*, and the detector data is shifted from left to right through shift register or tapped delay line 154*e*. Each output of register 154*d* is multiplied by a corresponding output of shift register or tapped delay line 154*e*, and the resulting products are summed by summation device 154*f*. The output of summation device 154*f* will be at a maximum when the data in shift register or tapped delay line 154*e* is best correlated with the reference data. Once the amount of shift required to produce this maximum is known, the appropriately shifted detector output data can be processed as shown in FIG. 12** and described above to determine whether or not any of the detector output data deviates unacceptably from the corresponding reference data.

All of the foregoing signal processing can be readily done in either analog or digital mode, as well as in either serial or parallel mode.

Figure 14A:
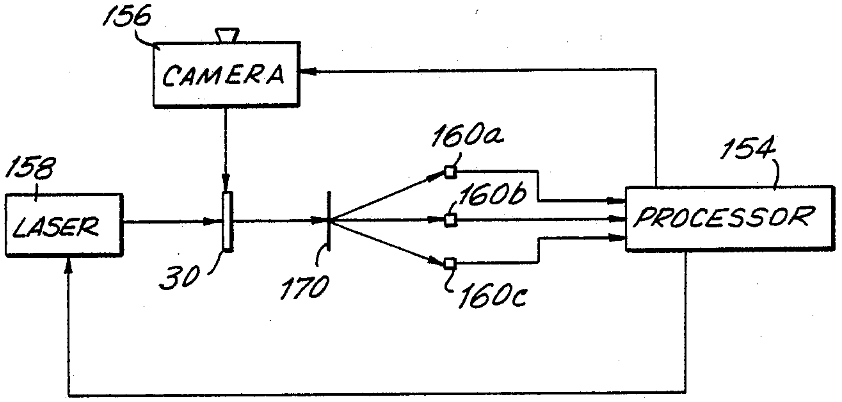
FIGS. 14A–C and 15–19 are simplified schematic block diagrams showing other alternative embodiments of portions of the apparatus of FIG. 9.

FIG. 14A shows a way in which portions of the optical system of FIG. 9 can be modified to produce several one-dimensional images in parallel. In FIG. 14A, computer-generated hologram ("CGH") 170 takes the place of rotating Dove prism 120 and cylindrical lens 42. CGH 170 is a well-known type of device which employs a pattern of data on an otherwise transparent, usually planar medium to locally modulate and spatially deflect different portions of the input light waves passing through the medium. As the name CGH implies, the pattern of data is determined by well-known computerized algorithms, and can be selected to cause the CGH to act as any of a wide variety of optical devices or systems. In particular, when the image of product 10 on display 30 is momentarily illuminated by laser 158 as described above in connection with FIG. 9, CGH 170 causes the light from display 30 to simultaneously form three different one-dimensional images of the display image. Thus this CGH acts like three differently rotated cylindrical lenses. Each of these one-dimensional images has the optical orientation of a respective one of the three one-dimensional images described above in connection with FIG. 9, and each is formed at the location of a respective one of detectors **160*a–c*. Because of the design flexibility of CGHs, these one-dimensional images can have any of a wide range of locations and orientations. Each of detectors 160*a–c* may be similar to detector 160 in FIG. 9 (e.g., made up of a plurality of small detector components 162 as shown in FIG. 10). The output signals of all of detectors 160*a–c* are applied to processor 154 for processing as described above in connection with FIG. 9, etc. In other respects, the embodiment of FIG. 14A may be similar to the embodiments of FIGS. 9 or 11**.

The CGH embodiment of FIG. 14A may have certain advantages over the lens embodiment of FIG. 9. It does not require any moving mechanical parts (e.g., a rotating Dove prism) and may therefore be cheaper to build, operate, and maintain. It is also faster because all three one-dimensional images are formed simultaneously, and as a result, the data for all three images are available simultaneously. If processor 154 has three parallel data processing channels, all three one-dimensional images can be analyzed simultaneously. On the other hand, the lens embodiment of FIG. 9 has the advantage of flexibility in that any number of one-dimensional images having any desired optical orientations can be formed merely by appropriate rotation of Dove prism 120. In FIG. 14A, CGH 170 must be changed for different products that require different one-dimensional images at different angles. FIG. 9 also has a cost advantage in that only one detector 160 is required.

Figure 14B:
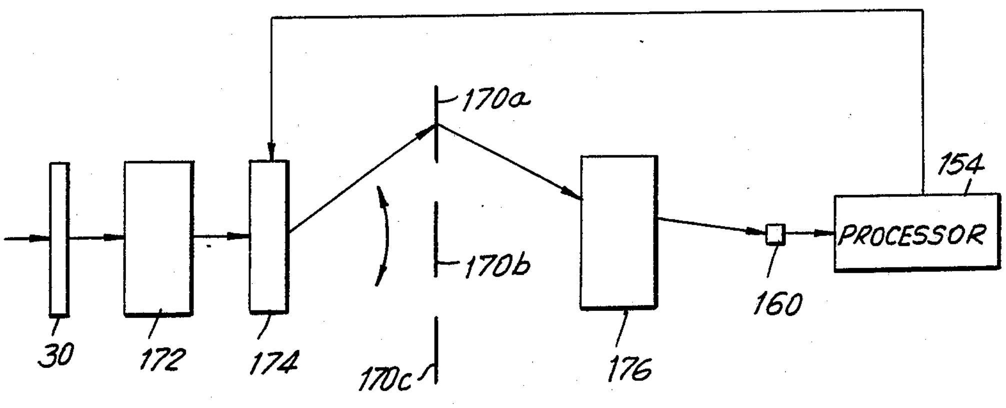

Because the processor 154 that must analyze the one-dimensional images generally limits the speed at which products can be processed, the embodiment shown in FIG. 14B may in some cases be more economical than the embodiment shown in FIG. 14A. In FIG. 14B, the two-dimensional input image from display 30 is imaged onto deflector 174 by conventional imaging optics 172. Deflector 174 (e.g., a mirror pivoted by a galvinometer controlled by processor 154) deflects the light from imaging system 172 to a selected one or a selected sequence of CGHs 170*a, b, c*, each of which forms a predetermined one-dimensional image applied to detector 160 by conventional imaging optics 176. The output signal or signals of detector 160 are applied to processor 154 as described above in connection with FIGS. 9 and 10. Accordingly, any one of several one-dimensional images can be selected by appropriate positioning of deflector 174. Alternatively, any desired sequence of one-dimensional images can be selected by appropriately sequencing the position of deflector 174. The set of CGHs 170 could be large enough to satisfy several different product inspection applications, so that the apparatus could be adapted for each different application merely by causing processor 154 to control deflector 174 as required for the current application.

Figure 14C:
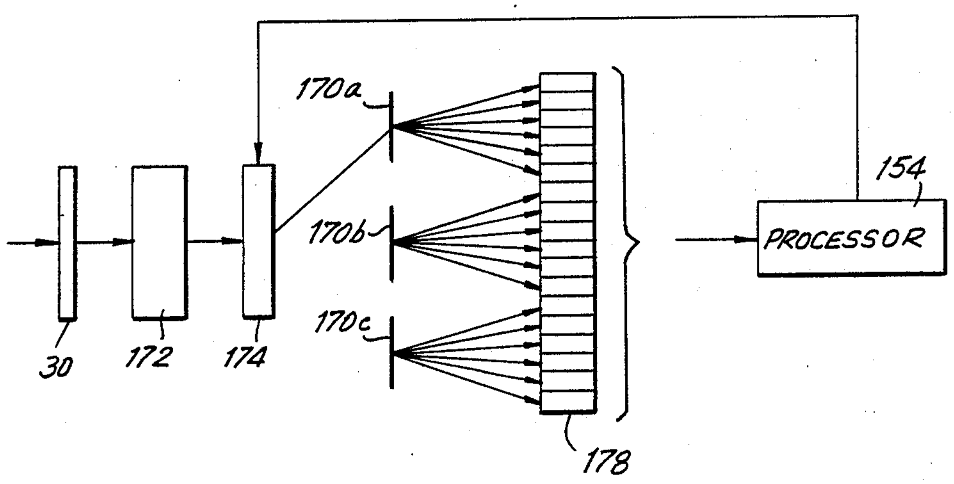

FIG. 14C shows another possible embodiment. In FIG. 14C (in which elements 30, 172, and 174 are similar to the corresponding elements in FIG. 14B), each CGH 170 produces several one-dimensional images, each of which is focused on a respective row (perpendicular to the plane of the paper in FIG. 14C) of two-dimensional detector array 178 (e.g., a conventional video camera). The product inspection problem being addressed determines which horizontal lines (i.e., one-dimensional images) from detector array 178 are used by processor 154. FIG. 14B uses a deflector 174 and one linear detector 160, while FIG. 14C uses a combination of a deflector 174 and several frequency-multiplexed CGHs 170 in several spatial locations to produce a large number of different one-dimensional images (i.e., N1×N2 images, where N1 is the number of CGHs and N2 is the number of one-dimensional images produced by each CGH) on a two-dimensional detector array 178. Cost and the requirements of the product inspection application will determine which of these systems is best in a particular application.

Figure 15:
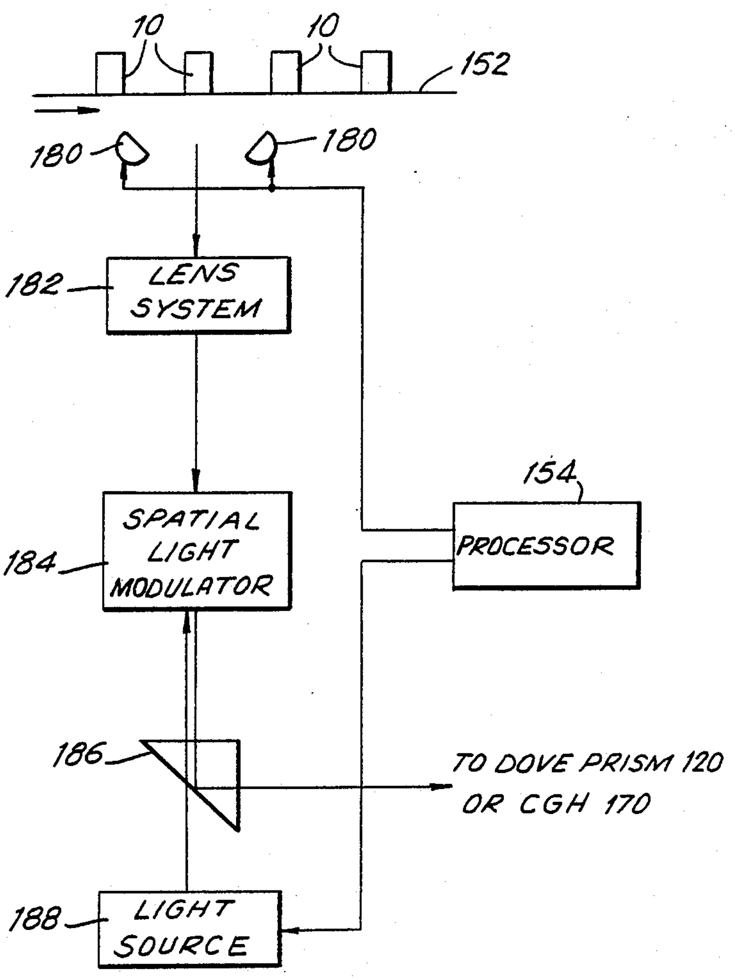

Another way to form a two-dimensional image of product 10 is shown in FIG. 15. Each time a product 10 is opposite lens system 182, processor 154 causes light sources 180 to momentarily illuminate the product. Light sources 180 can be conventional incoherent light sources such as strobe lights. Lens system 182 focuses the light reflected from product 10 (i.e., a two-dimensional image of product 10) on the input surface of spatial light modulator ("SLM") 184. SLM 184 is a conventional device which reflects light from its output surface only opposite points on its input surface which are illuminated by light from lens system 182. (Alternatively, SLM 184 can be made to reflect light from its output surface only opposite points on its input surface which are not illuminated by light from lens system 182.) Thus at approximately the same time that processor 154 activates light sources 180, processor 154 also activates light source 188 (e.g., a laser, light emitting diode, etc.). Coherent light from light source 188 passes through conventional beam splitter 186 and impinges on the output surface of SLM 184. This light is reflected back to beam splitter 186 only where the output surface of SLM 184 is reflective. The light returned to beam splitter 186 is reflected off to Dove prism 120 (if the remainder of the apparatus is as shown in FIG. 9) or to CGH 170 (if the remainder of the apparatus is as shown in FIG. 14A). The apparatus of FIG. 15 eliminates the need for camera 156 (which typically requires time for image scanning) and allows the entire image of the product to be formed in parallel.

In FIG. 15, SLM 184 and light source 188 can be omitted, but in that event imaging system 182 must ensure that nearly parallel (i.e., collimated) light enters Dove prism 120. The Dove prism and one-dimensional integrating optics produce the necessary one-dimensional image even with polychromatic (i.e., multiple wavelength) non-coherent light. Light sources 180 are typically (although not necessarily) polychromatic to ensure that different lines (on product 10) in different colors are all input with no attenuation. One reason for including SLM 184 and light source 188 would be to provide an amplification of the light level entering the Dove prism system. On the other hand, a CGH system (as in FIG. 14A) requires coherent light, so that in that case, light source 188 must be a laser.

Figure 16:
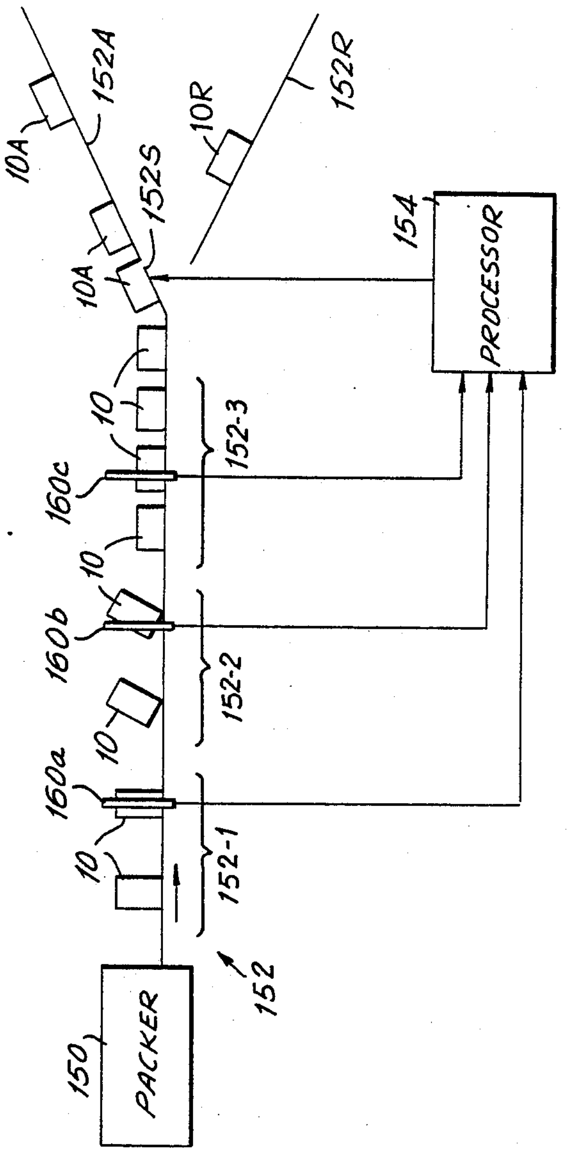

FIG. 16 shows yet another way in which several one-dimensional images of a product can be formed. In FIG. 16, products 10 emerge from packer 150 with an upright orientation and are conveyed to the right by conveyor 152. While still upright on conveyor portion 152-1, each product 10 passes detector 160*a* which may be generally similar to detector 160 in FIG. 10 with the longitudinal axis 46 of the detector perpendicular to the axis of motion of conveyor 152. Each photodetector 162 in detector 160*a* receives light from a narrow horizontal slice of the product 10 passing the detector and produces an output signal proportional to the integral of the light received from that slice. Processor 154 controls the integration time of detector 160*a* based on system synchronization and/or product location detection techniques similar to those described above in connection with FIG. 9. Accordingly, the output signal (serial) or signals (parallel) of detector 160*a* after a product 10 has passed the detector are similar to the output signal or signals of detector 160 in FIG. 9 with Dove prism 120 at a particular angular orientation. In particular, optically detectable horizontal lines on product 10 will cause peaks in the output signal or signals of detector 160*a* which can be used by processor 154 as described above in connection with FIG. 9, etc., to determine the acceptability of product 10.

After passing detector 160*a*, each product 10 enters conveyor portion 152-2 which reorients the product so that other optically detectable straight line segments on product 10 are parallel to the axis of motion of conveyor 152. While on conveyor portion 152-2, the reoriented product moves past detector 160*b*, which is similar to detector 160*a* in construction, orientation, and operation. Accordingly, the output signal or signals of detector 160*b* are representative of another one-dimensional image of product 10 and can be applied to processor 154 for processing as described above.

After passing detector 160*b*, each product 10 enters conveyor portion 152-3 which further reorients the product so that still other optically detectable straight line segments (in particular, initially vertical segments) are now horizontal and therefore parallel to the axis of motion of conveyor 152. While on conveyor portion 152-3, each product 10 moves past detector 160*c*, which is again similar in construction, orientation, and operation to detector 160*a*. Accordingly, detector 160*c* provides an output signal or signals (applied to processor 154) representative of a third one-dimensional image of each product 10.

If processor 154 finds that any of the one-dimensional images of a product 10 are unacceptable, processor 154 controls conveyor portion 152S to divert the unacceptable product 10R to conveyor portion 152R. Otherwise, processor 154 controls conveyor portion 152S to direct acceptable products 10A to conveyor portion 152A.

Although in the particular embodiment shown in FIG. 16 detectors 160 are stationary while products 10 move, those skilled in the art will appreciate that all that is required is appropriate relative motion between the detectors and the products, and that this can be accomplished with moving detectors and stationary products or with both the products and the detectors moving.

Figure 17:
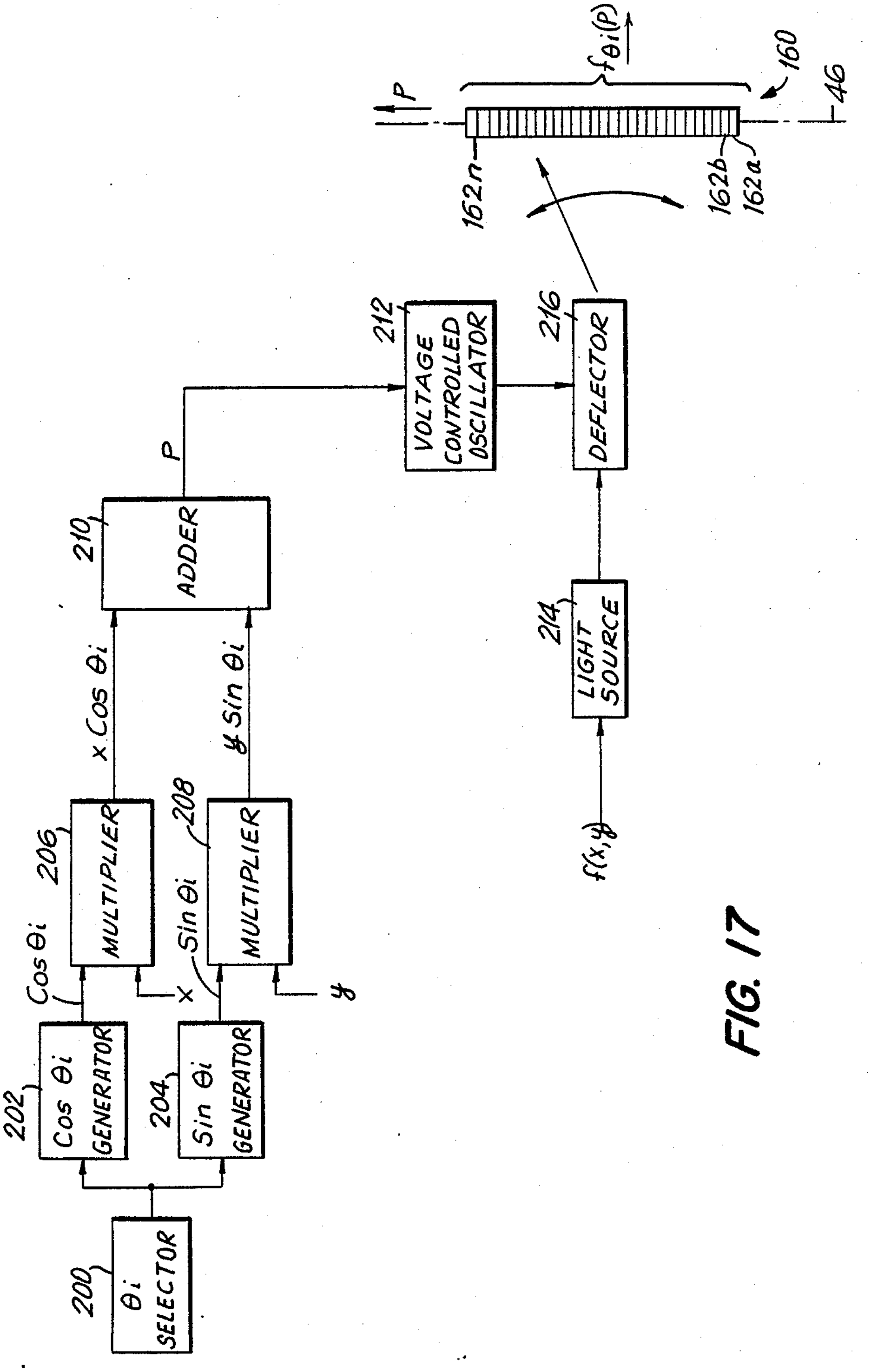

FIG. 17 shows yet another way in which one-dimensional images having any angular orientation $\theta i$ can be produced without the need for moving parts (as in FIG. 9), replacement of CGHs (as in FIG. 14), or possibly complicated relative motions of the products and detectors (as in FIG. 16). In other words, the apparatus of FIG. 17 allows a different angle of orientation for the one-dimensional image simply by selecting $\theta i$ by means of $\theta i$ selector 200, which can be a simple analog or digital selector (e.g., a rotary dial or a numeric keypad).

Underlying FIG. 17 is the principle that a one-dimensional image at angle $\theta i$ is a mapping of two-dimensional input image f(x,y) into a one-dimensional image $f\theta i(p)$, where p is derived as follows:

$$p = x \cos \theta i + y \sin \theta i \qquad (1)$$

For a given value of $\theta i$, Equation (1) gives the coordinate p in the one-dimensional image to which the input image intensity value f(x,y) at input image coordinates x and y maps. (For convenience in implementation, the x and y origin is assumed to be at the center of the image, and the range of $\theta i$ is assumed to be from 0 to $\pi$. As a result, p can be positive or negative.) In response to selection of $\theta i$ by way of selector 200, and to input signals x and y (which are typically ramp, sawtooth, or step-function signals of the type used to perform a raster scan in a video camera or other similar two-dimensional imaging device), the upper portion of the apparatus shown in FIG. 17 produces an output signal (applied to voltage controlled oscillator 212) proportional to the value of p given by Equation (1). In particular, the $\theta i$ output signal of selector 200 is applied to $\cos\theta i$ generator 202 and to $\sin\theta i$ generator 204. These elements (which may be table look-ups in processor 154) produce constant output signals respectively proportional to the cosine and sine of the selected value of $\theta i$. Multiplier 206 multiplies the output signal of $\cos\theta i$ generator 202 by the x raster scan signal, while multiplier 208 multiplies the output signal of $\sin\theta i$ generator 204 by the y raster scan signal. The output signals of multipliers 206 and 208 are added together in adder 210 to produce the above-described signal proportional to p.

As an alternative implementation of the upper portion of FIG. 17, the entire sequence of p values for any given value of $\theta i$ (associated with a given x,y input sequence) could be precomputed, output from a digital memory, and converted to analog form to produce the signal p. This alternative is discussed in greater detail below in connection with FIG. 19.

The lower portion of the apparatus shown in FIG. 17 uses the p output signal to actually map the input image intensity information f(x,y) into a one-dimensional output image detected by detector 160 (similar to the above-described detectors 160). In particular, the input image intensity signal f(x,y), which may be produced by the above-mentioned raster scan of a video camera (e.g., camera 156 in FIG. 9) or another similar two-dimensional imaging device, modulates the output of light source 214 (e.g., a laser or light emitting diode). Light from light source 214 is applied to deflector 216 (e.g., a conventional acousto-optical device) which deflects the applied light by an amount proportional to the frequency of the signal applied to it by voltage controlled oscillator 212. That frequency is in turn proportional to the magnitude of the p output signal of adder 210. Note that the p and f(x,y) signals are synchronized with one another by virtue of the fact that the same x and y raster scan signals are used to generate both p and f(x,y). Accordingly, at the end of one complete raster scan of the two-dimensional input image, photodetectors 162 will have received and accumulated optical information representative of a one-dimensional image of the input image at angle $\theta i$. Detector 160 can then be read out and the resulting signal or signals processed as described above in connection with FIG. 9, etc.

In FIG. 17 the angle $\theta i$ can be changed simply by using selector 200 to change $\theta i$. If several one-dimensional images are required simultaneously (as in FIG. 14A), the apparatus of FIG. 17 can be duplicated as many times as necessary to produce the required multiple one-dimensional images.

Figure 18:
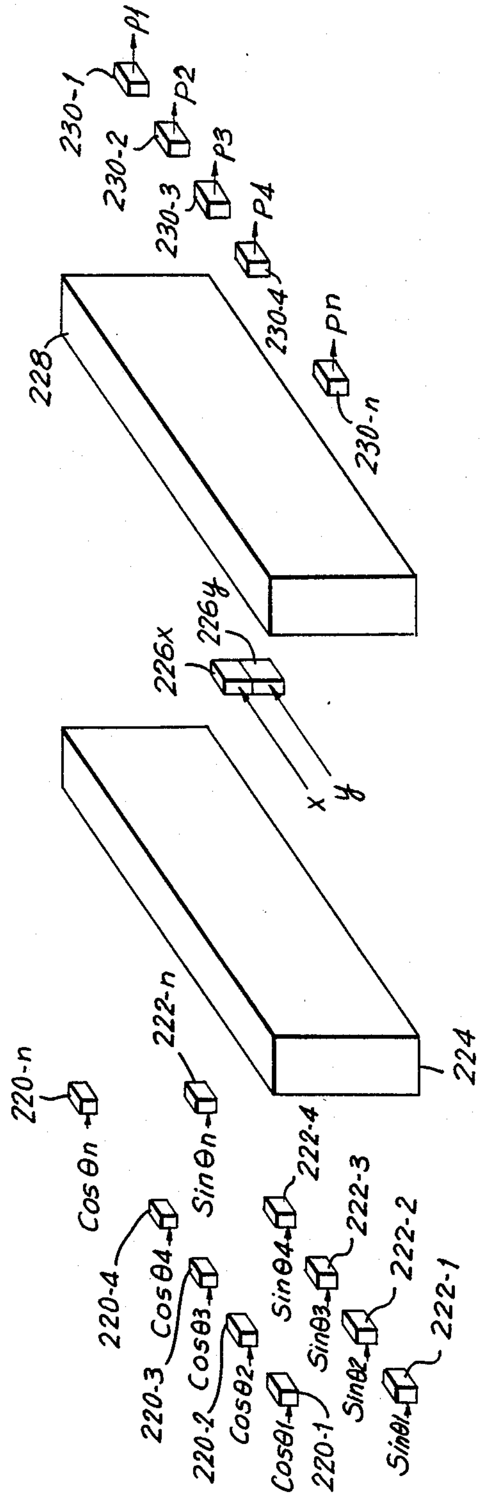

If desired, the upper portion of FIG. 17 can be implemented optically as shown in FIG. 18. Indeed, the apparatus of FIG. 18 has the capability of simultaneously generating a large number of values of p respectively associated with a corresponding number of values of $\theta i$. Thus FIG. 18 is equivalent to several duplications of the upper portion of FIG. 17.

In FIG. 18, each of elements 220 and 222 is a light source such as a laser or light emitting diode. The brightness of each of these devices is controlled by the applied signal (e.g., $\cos\theta 1$ in the case of light source 220-1). The various Cos and Sin signals applied to these devices are produced by signal generators similar to elements 202 and 204 in FIG. 17. For example, $\theta 1$ may be selected to be 0°, in which case the signal applied to light source 220-1 has a relative value of 1, while the signal applied to light source 222-1 has a relative value of 0. 82 may be selected to be 30°, in which case the signal applied to light source 220-2 has a relative value of 0.5, and the signal applied to light source 222-2 has a relative value of 0.866. To handle bipolar sine and/or cosine values, the input signals to light sources 220 and 222 can be biased to always be positive, and the bias can then be subtracted from the outputs of the system (i.e., from the outputs of detectors 230). Because the bias is known, correcting for it at the output is straight-forward. Bipolar x and y data applied to modulator devices 226 can be similarly biased.

Optical system 224 (which can be made up of conventional optical elements such as lenses) focuses all of the light produced by light sources 220 on modulator **226*x*, and similarly focuses all of the light produced by light sources 222 on modulator 226*y*. Each of devices 226 is similar to device 216 in FIG. 17, except that the frequency of the x and y raster scan signals respectively applied to devices 226*x* and 226*y* is constant while the amplitude of those signals varies. This multiplies the light input ($\cos\theta i$ and $\sin\theta i$) by x and y respectively. Optical system 228 (which can again be made up of conventional optical elements such as lenses) focuses the light from both of elements 226 vertically, and images light sources 220 and 222 horizontally onto a single row of detectors 230. Thus, for example, the light from light sources 220-1 and 222-1 is ultimately focused on detector 230-1. The vertical integration performed by optical system 228 achieves the addition required by Equation (1). The output signal of each detector 230 is therefore the p value (according to Equation (1)) for the associated value of $\theta$. Thus the apparatus of FIG. 18 is capable of simultaneously computing n signals p, each of which can be applied to apparatus of the type shown in the lower portion of FIG. 17** to produce output data $f\theta i(p)$ for a one-dimensional image having the orientation of the associated value of $\theta$.

It will be apparent from the foregoing discussion of FIGS. 17 and 18 that, if desired, the signal p for any given value of $\theta$ can be computed or otherwise determined in advance, assuming that the x and y signals are also known in advance (as they generally will be). Thus, the p signals for any values of $\theta$ can be computed in advance, stored in a memory, and read out as needed.

Figure 19:
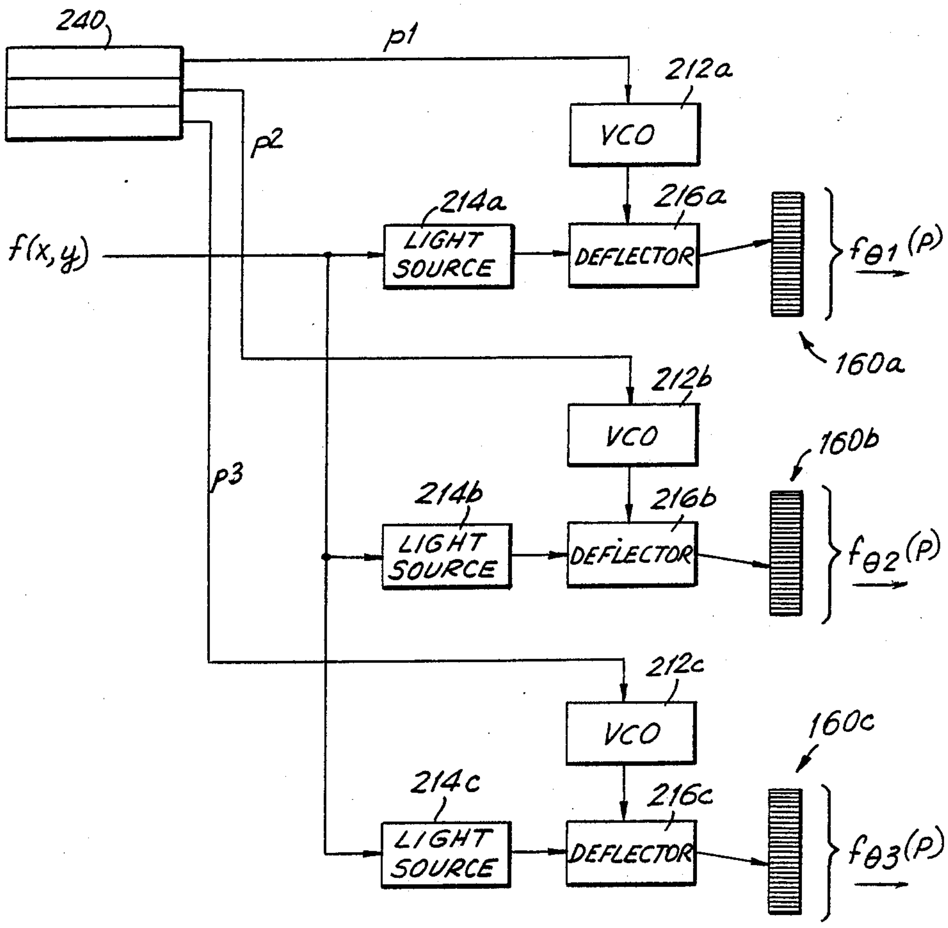

When several p sequences are available in parallel, the lower part of FIG. 17 can be modified as shown in FIG. 19. In this FIG. the p signals (p1 , p2, and p3) for three different values of $\theta$ ($\theta 1$, $\theta 2$, and $\theta 3$) are stored in memory 240. (Alternatively, these three p signals could be produced in parallel by apparatus of the type shown in FIG. 18.) Each of these three signals is read out from memory 240 in synchronization with application of the input image intensity signal f(x,y). Each p signal is applied to a respective one of voltage controlled oscillators **212*a*, 212*b*, and 212*c*. The output signal of each voltage controlled oscillator is applied to a respective one of deflectors 216*a*, 216*b*, and 216*c*, each of which appropriately deflects light from the associated light source 214*a*, 214*b*, and 214*c* to the associated detector 160*a*, 160*b*, and 160*c*. (Alternatively, one light source 214 could be used and its output spread across all of deflectors 216 (which could be combined in one multichannel acousto-optic deflector cell).) To avoid smearing as the deflector moves the beam across the detector array, the light source or sources can be pulsed on with f(x,y) data for each sample of the image. When the entire input image intensity signal f(x,y) has been processed in this way, the output signal or signals of each detector 160 represent a one-dimensional image of the input image at the associated angle $\theta 1$, $\theta 2$, or $\theta 3$. These output signals can be processed as described above in connection with FIG. 9**, etc., to determine the acceptability of the product associated with the input image.

Figure 20:
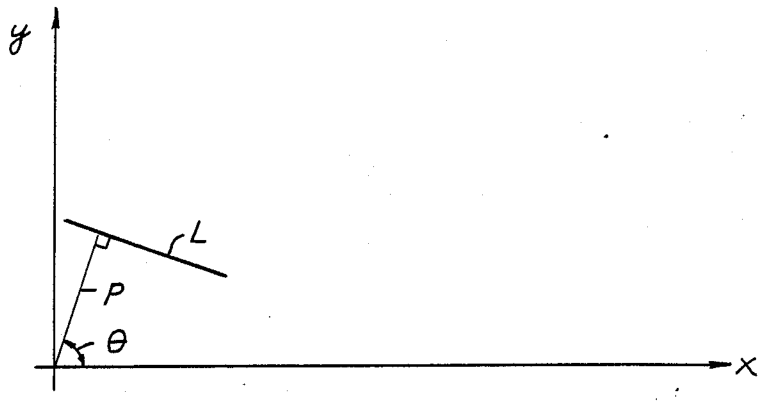
FIGS. 20 and 21 are diagrams which are useful in explaining the mathematical principles employed in the practice of this invention.
Figure 21:
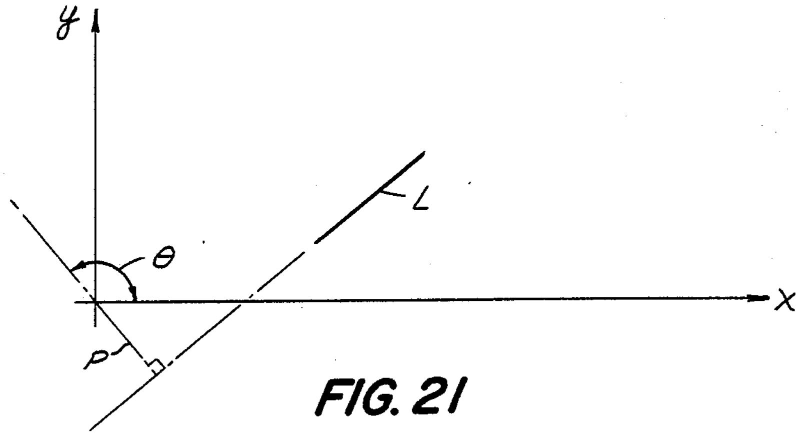
Figure 22:
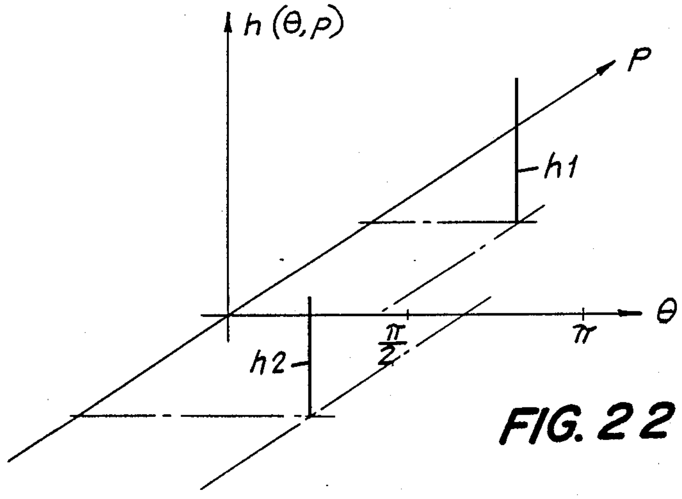
FIG. 22 is a depiction of the three-dimensional transformation (i.e., the Hough transform) of the graphic information contained in FIGS. 20 and 21 in accordance with the mathematical principles employed in the practice of this invention.

Underlying the phenomenon of producing one-dimensional images from two-dimensional images is the so-called Hough transform. The Hough transform of a two-dimensional image f(x,y) is described by:

$$h(\theta,p)=\int\int f(x,y)\delta(p-x \cos\theta-y \sin\theta)dxdy \quad (2)$$

where f(x,y) is the intensity of the input image at coordinates x and y, and $\delta(p-x\cos\theta-y\sin\theta)$ is a delta function which is one when $p-x\cos\theta-y\sin\theta$ is zero and zero for all other values of $p-x\cos\theta-y\sin\theta$. Thus the Hough transform maps all input image points (x,y) to sinusoids as in Equation (1). In accordance with Equation (2), the transformation in Equation (1) is performed for all image points (with the outputs weighted by the intensity of the input image point), and the results are accumulated in what is referred to as a Hough array $h(\theta,p)$. For present purposes, a possibly more useful view of the Hough transform of Equation (2) is that it maps straight lines in the input image to points in the Hough space. Each straight line L in the input image can be described by its normal distance p from the origin and the angle $\theta$ of this normal with respect to the x axis (see FIG. 20). (For completeness, FIG. 21 shows another example of how p and $\theta$ are determined. In this case p is negative.) Thus, each line L appears as a peak at coordinates ($\theta$,p) in the Hough space (see FIG. 22), with the height of the peak being proportional to the length of line L or the number of pixels on the line and their intensities. For example, peak h1 in FIG. 22 is due to line L in FIG. 20, and peak h2 in FIG. 22 is due to line L in FIG. 21. The use of the Hough transform to detect lines in an input image is well known (see Hough U.S. Pat. No. 3,069,654, although that patent uses slope-intercept parameters rather than the normal-angle parameters described above).

Note that the Hough space is typically bounded: p is limited by the size of the input image; and for values of $\theta$ greater than $2\pi$, $h(\theta,p)$ merely repeats. With optically generated Hough space procedures, it is convenient to limit $\theta$ to values from 0° to 180°, and to allow p to be bipolar as illustrated by FIGS. 20–22.

The one-dimensional images described above (e.g., those shown in FIGS. 5–7) are slices of the Hough space at various values of $\theta$. In particular, the horizontal and vertical axes in each of these FIGS. are respectively parallel to the p and $h(\theta,p)$ axes in FIG. 22. FIG. 5 is a slice of the Hough space taken at $\theta=0°$; FIG. 6 is a slice of the Hough space taken at $\theta=90°$; and FIG. 7 is a slice of the Hough space taken at $\theta=60°$.

From the foregoing, it will be seen that the rotating Dove prism apparatus of FIG. 9 is capable of forming the entire Hough transform of the input image. Each angular position of Dove prism 120 produces one constant-$\theta$ slice of the Hough space, so that when the Dove prism has rotated through an angle of 180°, all of the slices needed to form the entire Hough space will have been formed in sequence. If desired, processor 154 can collect data representative of the entire Hough space (or any number of constant-$\theta$ slices of that space) by appropriate sampling and storage of the output signals of detector 160.

Figure 23:
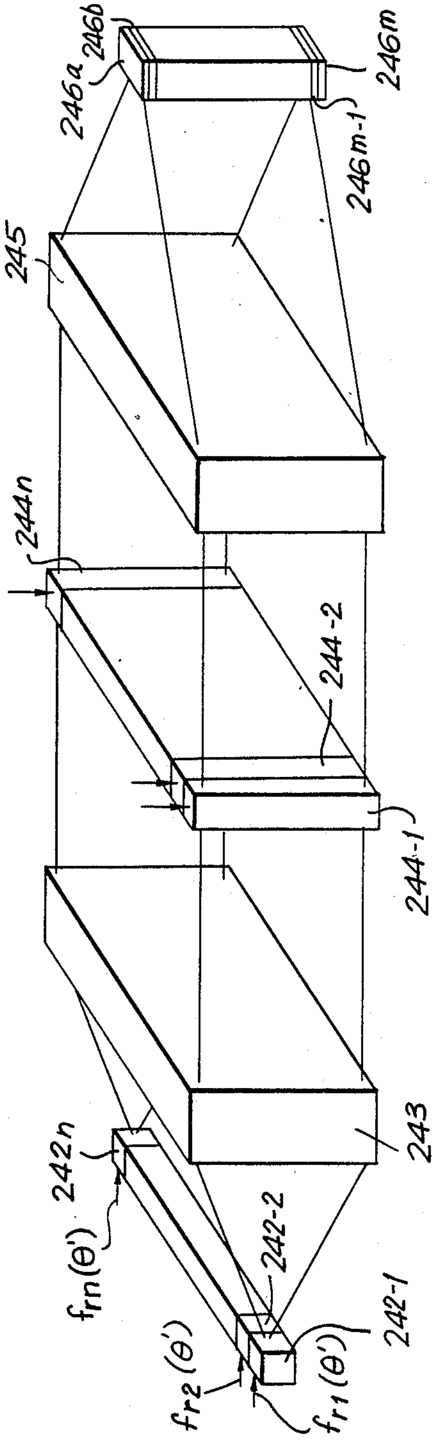
FIG. 23 is a block diagram of apparatus which can be used to produce data of the type shown in FIG. 22.

Another (faster) way to produce the entire Hough space is shown in FIG. 23. The polar coordinate form of Equation (1) is:

$$p=r \cos(\theta-\theta') \quad (3)$$

where p and $\theta$ are the same as in Equation (1), and r and $\theta'$ are the polar coordinates. Assuming that f(x,y) has also been transformed to polar coordinate form $f(r,\theta')$, the polar coordinate form of Equation (2) is:

$$h(\theta,p)=\int\int f(r,\theta')\delta(p-r \cos(\theta-\theta'))drd\theta' \quad (4)$$

f(x,y) can be rendered in polar form $f(r,\theta')$ by the simple expedient of using a camera 156 with a polar coordinate raster scan or by a computer generated hologram. From Equations (3) and (4) it can be seen that the mapping required from a polar $f(r,\theta')$ space to the Hough space is shift-invariant in $\theta$. This allows for a correlation acousto-optic realization of the Hough transform that will now be explained.

In FIG. 23, each point light source 242 (e.g., a light emitting diode or laser) receives a signal proportional to a respective one of a plurality of constant-r slices of $f(r,\theta')$, and produces light having intensity proportional to the level of the applied signal. The signals applied to light sources 242 can be derived, for example, from a polar coordinate scanning camera 156 as described above. Optical system 243 distributes the light from each light source 242 uniformly over the vertical dimension of a respective one of deflector channels 244. Each deflector channel 244, which may be an acousto-optic device similar to deflectors 216 in FIGS. 17 and 19, has applied to it $r\mathrm{Cos}\theta$ waveforms, where the amplitude of each cosine varies with the r value fed to the associated light source 242. (Alternatively, the r modulation can be included in the signals applied to light sources 242.) For each $fri(\theta')$ input point, the corresponding acousto-optic channel 244-*i* produces a one-dimensional output on detectors 246 that is the appropriate mapping specified by the function in Equation (4). Optical system 245 focuses the light from all of deflector channels 244 onto a single vertical array of m photodetectors 246, each of which corresponds to one point in the Hough array $h(\theta,p)$. These mappings are accumulated for all input image points $f(r,\theta')$, and this time integration on detectors 246 achieves the products and sums in Equation (4). The deflections produced by devices 244 are vertical. Optical system 245 sums these for all values of r onto detectors 246, and time integration on detectors 246 forms the sum for all values of $\theta'$. Thus Equation (4) is realized and the one-dimensional output on detectors 246 is the desired two-dimensional Hough transform lexicographically ordered on the one-dimensional detectors 246. Note that the inputs to light sources 242 are $\theta'$ outputs for fixed r values, i.e., a polar scan read-out of different r lines in parallel. With the polar transform, each point (a different $\theta'$ polar transform value), i.e., a circular scan of the original image at a fixed r value, maps to a cosine in the two-dimensional $(\theta,p)$ space. The mapping function is the same for each input point, with a shifted version of the same mapping function used for subsequent $\theta'$ values at the same r value. This shift-invariant property makes it possible to use an acousto-optic cell (like 244 in FIG. 23) to implement the required operation. FIG. 23 uses this concept involving viewing the transformation required as a mapping function. With the polar transformation, each input image point (a new $\theta'$ value for a fixed r) maps to a sinusoid in a two-dimensional $(\theta,p)$ space. If the two-dimensional sinusoid mapping is scanned horizontally, the two-dimensional sinusoid in $(\theta,p)$ space is lexicographically ordered into a one-dimensional vector with the p sequence for line $\theta 1$ followed by the p sequence for line $\theta 2$, etc. With this signal fed to the acousto-optic cell 244 of FIG. 23, the output of detector 246 is the sequence of p values for $\theta 1$, the sequence for $\theta 2$, etc. This scan format for the mapping function (i.e., horizontally, with successive $\theta$ line scans) allows utilization of the shift-invariant property of the mapping function as shown in Equations (3) and (4). Because the same signal is applied to each acousto-optic cell channel, the apparatus of FIG. 23 can be modified to use only one acousto-optic cell 244 and thus use a very viable processor architecture. The full power and generality of the system of FIG. 23 arises when generalized mappings or Hough transforms are employed. Accordingly, after one complete scan of $f(r,\theta')$, the output signal (serial) or signals (parallel) of detectors 246 are the complete Hough space data suitable for processing by processor 154 as described above or below.

If the size or scale of the input image changes by a factor s (e.g., because in FIG. 9 product 10 is slightly closer to or farther from camera 156 than expected), then the Hough transform of the scaled image and the Hough transform of the reference image are related by:

$$h_s(\theta,p/s)=h(\theta,p) \qquad (5)$$

where s is the scale factor. In other words, the Hough space is also scaled, but only parallel to the p axis. Thus a projection of the Hough space $h(\theta)$ parallel to the $\theta$ axis is scale-invariant.

If the input image rotates by an angle $\theta$ (e.g., because in FIG. 9 product 10 is tipped up one way or the other on conveyor 152), then the new and original Hough transforms are related by:

$$h_r(\theta,p)=h(\theta-\phi,p) \qquad (6)$$

In other words, the new Hough transform is a translated version of the original Hough transform, with the translation being parallel to the $\theta$ axis and proportional to the input image rotation $\phi$. In this case, a projection of the Hough space h(p) parallel to the p axis is invariant to rotation of the input object.

If the input image translates in any direction parallel to its plane (e.g., because in FIG. 9 product 10 is shifted left or right on conveyor 152 when its image is formed), then the new Hough space has the constant-$\theta$ slices shifted in the p direction, with a different (but easily calculated) amount of shift for each value of $\theta$. In particular, an input image translated by x1,y1 has a Hough transform with the original points $\theta$,p mapped to new points $\theta 1$,p1, where $$p1=p+t\ \mathrm{Cos}\ (\theta-\alpha) \text{ and } \theta 1=\theta \qquad (7)$$

where $$t^2=x1^2+y1^2 \text{ and } \alpha=\mathrm{Arctan}\ (y1/x1) \qquad (8)$$

From the foregoing it will be seen that if a projection of the Hough space is formed parallel to the $\theta$ axis (i.e., $h(\theta)$), the distribution of information in that one-dimensional projection is unaffected by translations of the input image parallel to its plane. $h(\theta)$ is also unaffected by scale changes in the object, but this is generally not of concern in product inspection applications. However, $h(\theta)$ will be shifted by an amount proportional to any rotation of the input image. Similarly, if a projection of the Hough space is formed parallel to the p axis (i.e., h(p)), the distribution of information in that projection is unaffected by rotation of the image.

These principles can be used in various ways in accordance with this invention to facilitate product inspection. For example, if the product is subject to translation and/or rotation relative to the sensor, and if $h(\theta)$ for an acceptable product is sufficiently distinctive, the apparatus of FIG. 9 can be used to form $h(\theta)$ as follows. As soon as the image of product 10 has been formed on display 30, processor 154 causes laser 158 to illuminate that image. Processor 154 then causes prism control 122 to rotate Dove prism 120 through an angle of 180° (equivalent to rotating the image 360°). As Dove prism 120 rotates, processor 154 periodically samples the output signals from photodetectors 162$a$–$n$ and inputs those signal samples to summation device 190 (FIG. 10). Summation device 190 sums the applied signal samples and applies the result to processor 154. (Alternatively, this integration of detector 162 outputs could be produced optically by imaging the detector line down into one detector, i.e., by performing the integration optically in space.) Each summation signal sample is the sum over a particular constant-$\theta$ slice of the Hough space for the image. Collectively, the time history output for these successive summation signal samples comprises the $h(\theta)$ projection of the Hough space. If the product is acceptable and merely translated (not rotated), the resulting $h(\theta)$ curve will match the $h(\theta)$ curve for an acceptable product, and processor 154 will record that the product is acceptable. (Apparatus of the type shown in FIG. 12 can be used to determine whether or not such a match exists.) On the other hand, if the detected $h(\theta)$ curve does not match the corresponding curve for an acceptable product, processor 154 can either record that the product is unacceptable, or if product rotation is possible and permissible, processor 154 (using apparatus of the type shown in FIG. 13, and then possibly apparatus of the type shown in FIG. 12) can first attempt to match the detected and acceptable (reference) $h(\theta)$ curves by shifting (translating) either curve until a match is found or until all possible combinations have been unsuccessfully tried. If a match is found, processor 154 records that the product is acceptable. Otherwise, processor 154 records that the product is unacceptable.

Figure 13:
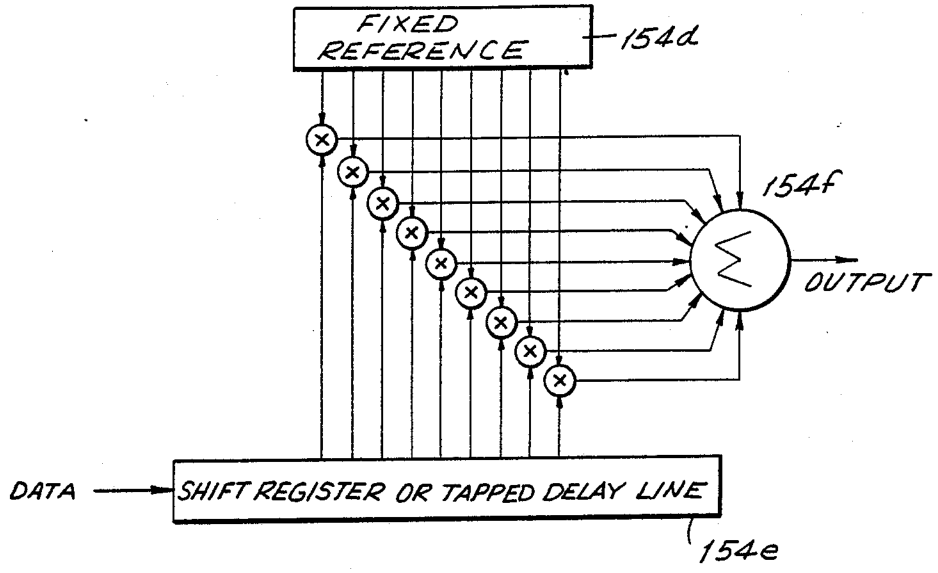
FIG. 13 is a schematic block diagram further showing how a portion of the apparatus of FIGS. 9–11 (and other subsequent FIGS.) may operate to analyze one-dimensional image data.

If it is desired to determine the amount by which product 10 is rotated, that can be determined from the process described immediately above, using apparatus of the type shown in FIG. 13. The amount by which either the detected or reference $h(\theta)$ curves must be shifted in order to produce a match between those curves indicates the rotational misalignment $\phi$ of the product (independent of its in-plane translation, and also independent of its scale as shown by Equation (5)).

Once $\phi$ has been determined as described immediately above, the two-dimensional Hough transform array can be corrected for rotation by shifting the data parallel to the $\theta$ axis by an amount equal to $\phi$.

With the Hough transform array data corrected for rotation, further analysis of that data is facilitated. For example, it is now possible to find among the constant-$\theta$ slices those that may be required for more detailed study in order to determine product acceptability. Thus, if the product must be tested against constant-$\theta$ slices such as those shown in FIGS. 5–7, but the product may be rotated, once the amount of rotation has been determined, the constant-$\theta$ slices corresponding to FIGS. 5–7 can be found in the two-dimensional Hough transform array data. Then each of these constant-$\theta$ slices is tested for acceptability as described above, and processor 154 records the acceptability or unacceptability of the product on that basis. This can either be done by having processor 154 collect and store all the individual output signals of detector elements 162 for different $\theta$ values, or by having processor 154 compute the angles to which Dove prism 120 must be rotated in order to offset the effect of product rotation and sampling the image on display 30 again with Dove prism 120 at those angles.

Another possible use of the two-dimensional Hough transform array data once it has been corrected for rotation as described above is to determine the amount x1 and y1 by which the object is translated horizontally and vertically, respectively. Assuming no scale change, then with the Hough space data corrected for rotation as described above, x1 and y1 can be determined as follows: Equations (7) and (8) show that translations of the input image result in translations in $h\theta i(p)$, i.e., the constant-$\theta$ slice of the Hough space at $\theta = \theta i$. To determine the two input translation parameters x1 and y1 (or equivalently $\alpha$ and t) in Equation (7), two columns $h\theta 1(p)$ and $h\theta 2(p)$ at different $\theta$ values are selected. Each of these two $h\theta i(p)$ signals is correlated with the associated reference pattern (e.g., using apparatus of the type shown in FIG. 13) to determine the shift required to align the $h\theta i(p)$ data and the associated reference patterns. Because two unknown parameters x1 and y1 (or $\alpha$ and t) must be determined, two such $h\theta i(p)$ correlations are required at different $\theta$ values. In practice, the $\theta$ lines at which the $h\theta i(p)$ patterns are obtained should be lines including significant data peaks. If desired, better estimates of x1 and y1 (or $\alpha$ and t) can be developed if more than two $h\theta i(p)$ correlations are performed. Once the shifts required to align the selected $h\theta i(p)$ columns are known, those values are used to solve Equations (7) and (8) for $\alpha$ and t and then x1 and y1. When x1 and y1 have been determined in this manner, all or any portion of the Hough transform array data can be corrected for shift using Equations (7) and (8).

The above-described one-dimensional Hough transform projection processing provides estimates of product rotation $\phi$ and translation x1, y1, as well as Hough transform array data $h(\theta,p)$ corrected for these distortions. Analysis of the projections $h(p)$ and $h(\theta)$ can also determine product acceptability as discussed above in the case of $h(\theta)$ and as will now be discussed in the case of $h(p)$.

The one-dimensional projection $h(p)$ is useful in certain product inspection applications. For example, if the input image has a relatively small number of straight lines and edges, and it is desired to determine parallelism between two such features, it may not be necessary to search for the particular constant-$\theta$ slice in which those two features produce two appropriately spaced peaks. Instead, it may be sufficient to simply form $h(p)$ (which is a superposition of all constant-$\theta$ slices and which is therefore insensitive to image rotation) and to look for the required two spaced peaks in that curve.

Once again the apparatus of FIG. 9 can be used to determine $h(p)$. Processor 154 operates Dove prism 120 and laser 158 as described above in connection with determining $h(\theta)$. Instead of using summation device 190 (FIG. 10), however, electronic integrators 192*a–n* are used to separately integrate the output signals of each of detector components 162*a–n* throughout the 180° rotation of the Dove prism. (Alternatively, the temporal integration can be done directly in each detector element 162*a–n*.) At the completion of the Dove prism rotation, the output signal of each integrator 192 represents one constant-p slice of the Hough space. Collectively, these integrator output signals are $h(p)$. Processor 154 compares this detected $h(p)$ curve to the reference $h(p)$ curve for an acceptable product (or otherwise analyzes the detected $h(p)$ curve for acceptability), and determines whether or not product 10 is acceptable on that basis.

If the input image is scaled, the $h(p)$ pattern is also scaled, but the relative displacement between peaks in $h(p)$ does not change. Thus, this is a fast and efficient inspection technique that will be suitable for many applications. If the input image is translated, each constant-$\theta$ slice of the Hough space is shifted differently, so the Hough array data must be corrected for translation (as described above) before $h(p)$ is formed for comparison with reference h(p) data. If the input image is merely rotated, h(p) is unaffected as has been mentioned.

The comparisons of various one-dimensional images that were referred to above can be performed electronically as described, for example, in connection with FIGS. 12 and 13. This type of comparison allows determination of whether or not any peak in the one-dimensional image deviates from a predetermined value by more than a predetermined amount. Product identification and acceptability can also be obtained by comparing the entire one-dimensional image to one or several one-dimensional references. This comparison involves a vector image product (i.e., the sum of the point-by-point product of the elements of the two one-dimensional signals). These vector image products can be performed for all relative shifts of the two one-dimensional signals. Such a shift search is needed when the object rotation $\phi$, translation x1, y1, etc., must be searched (i.e., when a one-dimensional correlation is required). The system of FIG. 24 achieves this.

Figure 24:
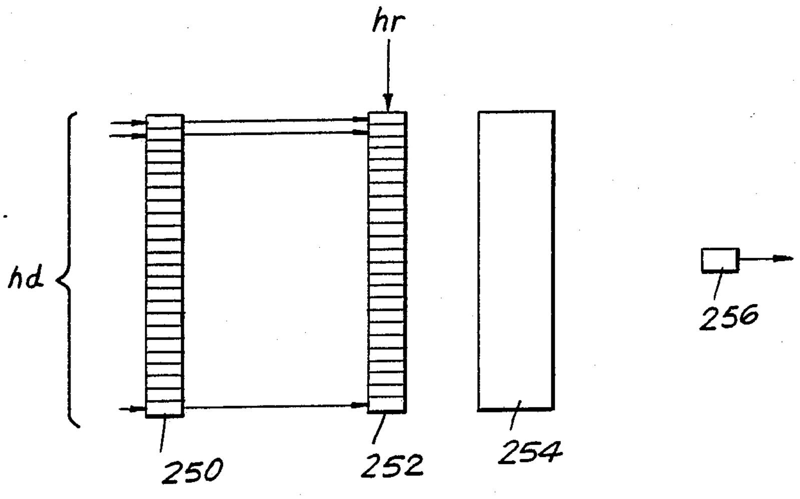
FIG. 24 is a block diagram of apparatus which can be used to process data of the type shown in FIG. 22.

In FIG. 24, a large number of samples of the possibly distorted Hough transform projection or slice hd are respectively fed in parallel to a corresponding number of light sources 250 (e.g., laser or light emitting diodes), each of which produces output light having intensity proportional to the level of the associated input signal. The light from each light source 250 is imaged onto a corresponding portion of acousto-optic cell 252. The reference pattern hr with which hd is to be correlated is serially applied in a cyclically repeating fashion to acousto-optic cell 252. The outputs of all of the segments of cell 252 are focused onto a single detector 256 by optical system 254 (made up of conventional optical elements such as lenses). Thus, the time-history output of detector 256 (which integrates the product of the light leaving light sources 250 and the contents of cell 252) is the correlation of hd and hr for all possible shifts or distortion parameters. Should several reference patterns be required, these can be frequency-multiplexed onto the hr input to cell 252, and the correlation of hd with each reference will appear on a respective one of several detectors 256 spaced vertically in FIG. 24. Alternatively, a multichannel acousto-optic cell can be employed for device 252. As still another alternative, a long one-dimensional pattern can be partitioned (in any single axis needed) among the several channels of the above-mentioned multichannel acousto-optic cell.

Note that the apparatus of FIG. 24 forms a vector image product (product and sum) of two one-dimensional signals. It thus compares two signals for all shifts between the two signals. This is a correlation (i.e., a vector image product for all shifts). The more detailed and specific product tests (for lengths of lines, etc.) should not be done with a correlator. Rather, these tests require checking the presence and height of each peak of interest. It is possible to correlate with an inverted reference signal. This subtracts the two signals and yields both positive and negative values, but the sum of such values can cancel out significant errors. Thus the system of FIGS. 12 and 13 is preferable for such cases.

Figure 25:
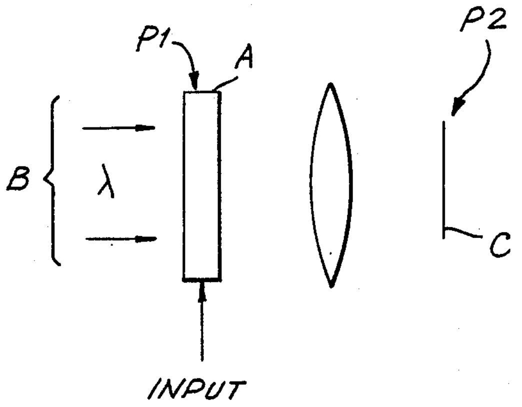
FIG. 25 is a simplified side view of apparatus which can be used to form a Fourier transform of Hough transform data.

From the central limit theorem, it is well-known that the one-dimensional Fourier transform of a slice of the Hough transform array data at a given value of $\theta$ is equivalent to a one-dimensional slice of the two-dimensional Fourier transform of the input image along an angle $\theta$ in the two-dimensional Fourier transform space. The one-dimensional Fourier transform can be produced optically or digitally by well-known methods, with the choice depending on the speed requirements and the cost and size of the implementation. FIG. 25 shows an acousto-optic one-dimensional Fourier transform system that achieves the spectrum of the one-dimensional signal fed to the acousto-optic cell at plane P1. The input signal to be Fourier transformed is fed to acousto-optic device A which is illuminated by a laser beam B and forms the Fourier transform of the input signal on a linear detector array C at plane P2. This architecture, when fed with the Hough transform of an input image, yields the one-dimensional Fourier transform of the input and thus a one-dimensional slice of the two-dimensional Fourier transform. Such one-dimensional Fourier transform slices have many uses in product inspection. For example, to confirm that certain lines of text or pattern are present on the product, that region of the object can be scanned to determine the presence of the pattern or text and the quality of it from a simple analysis of the one-dimensional Fourier transform. The angle of the one-dimensional Fourier transform slice can be selected depending on the orientation of this information in the image. For the case of text, it has characteristic spacings which appear as given Fourier transform frequency components. The detailed Fourier transform pattern analysis will be specific to particular inspection problems. In the case of cigarette inspection, the one-dimensional pattern for a given image scan can be correlated with reference patterns. For the case of warning label text on cigarette packs, such correlations can be achieved by conventional acousto-optic techniques.

I claim:

1. Apparatus for determining whether or not a product has predetermined optically detectable properties including first and second optically detectable straight line segments respectively having first and second predetermined intersecting orientations in a predetermined object plane comprising:

means for forming first and second one-dimensional images of said object plane for said product such that all straight line segments having said first predetermined orientation in said object plane are respectively integrated to points in said first one-dimensional image, and such that all straight line segments having said second predetermined orientation in said object plane are respectively integrated to points in said second one-dimensional image;

means for monitoring said first and second one-dimensional images to determine whether or not said one-dimensional images respectively include points having the image intensities that would result if said object plane for said product included said first and second straight line segments respectively having said first and second predetermined orientations; and means for producing an output indicative of whether or not said product has said predetermined optically detectable properties based on whether or not said first and second one-dimensional images respectively include points having said image intensities;

wherein said means for forming said first and second one-dimensional images comprises:

a single computer generated hologram for forming said first and second one-dimensional images at respective, spaced, first and second lines.

2. The apparatus defined in claim 1 wherein said means for monitoring said first and second one-dimensional images comprises:

first and second detector means for respectively detecting light at said first and second lines.

3. Apparatus for determining whether or not a product has predetermined optically detectable properties including first and second optically detectable straight line segments respectively having first and second predetermined intersecting orientations in a predetermined object plane comprising:

means for forming first and second one-dimensional images of said object plane for said product such that all straight line segments having said first predetermined orientation in said object plane are respectively integrated to points in said first one-dimensional image, and such that all straight line segments having said second predetermined orientation in said object plane are respectively integrated to points in said second one-dimensional image;

means for monitoring said first and second one-dimensional images to determine whether or not said one-dimensional images respectively include points having the image intensities that would result if said object plane for said product included said first and second straight line segments respectively having said first and second predetermined orientations; and means for producing an output indicative of whether or not said product has said predetermined optically detectable properties based on whether or not said first and second one-dimensional images respectively include points having said image intensities;

wherein said means for forming said first and second one-dimensional images comprises:

first and second computer generated hologram means respectively forming said first and second one-dimensional images;

deflector means for successively deflecting light from said object plane to said first and second computer generated hologram means; and means for focusing light from both of said computer generated hologram means to a single line.

4. The apparatus defined in claim 3 wherein said means for monitoring said first and second one-dimensional images comprises:

detector means for detecting light focused to said single line.

5. Apparatus for determining whether or not a product has predetermined optically detectable properties including at least one optically detectable straight line segment parallel to each of a plurality of different predetermined orientations in a predetermined object plane comprising:

a plurality of computer generated holograms;

deflector means for selectively deflecting light from said object plane to any one of said computer generated holograms, said one of said holograms responding by producing a plurality of one-dimensional images of said object plane, each of said one-dimensional images having a longitudinal axis perpendicular to a respective one of a corresponding plurality of said predetermined orientations, the one-dimensional images produced by each hologram being respectively disposed in a plurality of parallel, laterally spaced lines; and a plurality of detector means, each detecting the light received at a respective one of said parallel, laterally spaced lines.

6. Apparatus for determining whether or not a product has predetermined optically detectable properties including an optically detectable straight line segment parallel to a predetermined orientation in a predetermined object plane comprising:

means for forming a one-dimensional image of said object plane for said product such that all straight line segments parallel to said predetermined orientation in said object plane are respectively integrated to points in said one-dimensional image;

means for monitoring said one-dimensional image to determine whether or not said one-dimensional image includes a point having the image intensity that would result if said object plane for said product included said straight line segment parallel to said predetermined orientation; and means for producing an output indicative of whether or not said product has said predetermined optically detectable properties based on whether or not said one-dimensional image includes a point having said image intensity;

said means for forming a one-dimensional image including:

spatial light modulator means for receiving light from said object plane for said product and for modulating the reflectivity of an output surface in accordance with said light;

a light source for directing light to said output surface so that it will be reflected from said output surface in accordance with the reflectivity of said output surface; and means for focusing the light reflected from said output surface to said one-dimensional image.

7. The apparatus defined in claim 6 wherein said light source directs light to said output surface along an axis perpendicular to said surface, and wherein said means for focusing the light reflected from said output surface comprises:

beam splitter means disposed between said light source and said output surface for causing a portion of the light reflected from said output surface to be deflected away from said axis.

8. The apparatus defined in claim 7 wherein said means for focusing the light reflected from said output surface further comprises:

a cylindrical lens having a longitudinal axis parallel to said output surface and perpendicular to said predetermined orientation as said predetermined orientation appears in said portion of the light deflected by said beam splitter means, for focusing said portion of the light deflected by said beam splitter means to said one-dimensional image.

9. The apparatus defined in claim 7 wherein said means for focusing the light reflected from said output surface further comprises:

a Dove prism mounted for rotation about a rotational axis coincident with the axis along which said portion of the light deflected by said beam splitter means travels for producing an image of said portion of said light which is rotated by an amount which is a function of the angle of rotation of said Dove prism about said rotational axis;

means for focusing said rotated image to said one-dimensional image; and means for rotating said Dove prism to the angle which causes said predetermined orientation as it appears in said rotated image to be perpendicular to the longitudinal axis of said one-dimensional image.

10. The apparatus defined in claim 7 wherein said means for focusing the light reflected from said output surface further comprises:

computer generated hologram means for receiving said portion of the light deflected by said beam splitter means and for focusing said portion of said light to said one-dimensional image.

11. Apparatus for determining whether or not a product has predetermined optically detectable properties including an optically detectable straight line segment parallel to a predetermined orientation in a predetermined object plane comprising:

means for forming a one-dimensional image of said object plane for said product such that all straight line segments parallel to said predetermined orientation in said object plane are respectively integrated to points in said one-dimensional image;

means for monitoring said one-dimensional image to determine whether or not said one-dimensional image includes a point having the image intensity that would result if said object plane for said product included said straight line segment parallel to said predetermined orientation; and means for producing an output indicative of whether or not said product has said predetermined optically detectable properties based on whether or not said one-dimensional image includes a point having said image intensity;

said means for forming a one-dimensional image comprising:

means for scanning said object plane to produce an output signal sequentially representative of the intensity of the image at each point in said object plane;

a light source;

means for modulating the intensity of the light from said light source in accordance with said scanning means output signal; and deflector means for selectively deflecting the modulated light from said light source to selected ones of a plurality of points on a one-dimensional image line based on a predetermined mapping function between the points in said object plane and the points on said one-dimensional image line.

12. The apparatus defined in claim 11 wherein said deflector means comprises:

means for producing a mapping signal proportional to said mapping function; and means responsive to said mapping signal for deflecting the modulated light from said light source by an amount proportional to said mapping signal.

13. The apparatus defined in claim 12 wherein said mapping function is given by the equation $p=x \text{ Cos } \theta+y \text{ Sin } \theta$, where x and y are the object plane point coordinates, $\theta$ is dependent on the angle of said predetermined orientation, and p is the coordinate of the point on said one-dimensional image line.

14. The apparatus defined in claim 13 wherein said means for producing said mapping signal comprises:

means for storing said mapping function; and means for reading out the stored mapping function in synchronization with said scanning means.

15. The apparatus defined in claim 13 wherein said means for producing said mapping signal comprises:

means for producing first and second output signals respectively proportional to Cos$\theta$ and Sin$\theta$;

means for multiplying said first output signal by a signal proportional to the x coordinate of the object plane point being scanned by said means for scanning to produce a third output signal;

means for multiplying said second output signal by a signal proportional to the y coordinate of the object plane point being scanned by said means for scanning to produce a fourth output signal; and means for adding said third and fourth signals together to produce said mapping signal.

16. The apparatus defined in claim 13 wherein said means for producing said mapping signal comprises:

a first light source for producing light having intensity proportional to Cos$\theta$;

a second light source for producing light having intensity proportional to Sin$\theta$;

first means responsive to a signal proportional to the x coordinate of the object plane point currently being scanned by said means for scanning for multiplying the light from said first light source by an amount proportional to said x coordinate signal;

second means responsive to a signal proportional to the y coordinate of the object plane point currently being scanned by said means for scanning for multiplying the light from said second light source by an amount proportional to said y coordinate signal;

a photodetector; and means for focusing light from said first and second means toward said photodetector so that the light applied to said photodetector is proportional to the sum of the fractions of the light from said first and second light sourced reaching said photodetector via said first and second means.

17. The apparatus defined in claim 16 wherein said first and second means respectively comprise:

acousto-optic modulator means.

18. The apparatus defined in claim 12 wherein said means responsive to said mapping signal comprises:

acousto-optical deflector means.

19. Apparatus for determining whether or not a product has predetermined optically detectable properties including an optically detectable straight line segment in a predetermined object plane comprising:

means for forming a plurality of one-dimensional images of said object plane for said product, each one-dimensional image having a different angle of orientation parallel to said object plane;

means for separately integrating corresponding portions of all of said one-dimensional images to produce a respective projected value for each portion of said integrated one-dimensional images; and means for analyzing said projected values to determine whether or not said values include a predetermined value that would result if said object plane for said product included said straight line segment.

20. The apparatus defined in claim 19 wherein said means for forming a plurality of one-dimensional images comprises:

a Dove prism mounted for rotation about a rotational axis perpendicular to said object plane for producing an image of said object plane which is rotated by an amount determined by the angle of rotation of said Dove prism about said rotational axis;

means for focusing said rotated image to a one-dimensional image line; and means for rotating said Dove prism through a predetermined rotational angle to cause said plurality of one-dimensional images to form one after another in succession at said one-dimensional image line.

21. The apparatus defined in claim 19 wherein said means for forming a plurality of one-dimensional images comprises:

means for scanning said object plane to produce an output signal sequentially representative of the intensity of the image at each point in said object plane;

a light source;

means for modulating the intensity of the light from said light source in accordance with said scanning means output signal; and deflector means for selectively deflecting the modulated light from said light source to selected ones of a plurality of points on a one-dimensional image line based on a predetermined mapping function between the points in said object plane and the points on said one-dimensional image line, said mapping function being a function of the angle of orientation associated with each one-dimensional image.

22. The apparatus defined in claim 19 wherein said means for forming a plurality of one-dimensional images comprises:

computer generated hologram means.

23. Apparatus for determining whether or not a product has predetermined optically detectable properties including an optically detectable straight line segment in a predetermined object plane comprising:

means for forming a plurality of one-dimensional images of said object plane for said product, each one-dimensional image having a different angle of orientation parallel to said object plane, and each one-dimensional image including a plurality of image segments spaced along the longitudinal axis of said one-dimensional image;

means for separately integrating the image segment at each position along the longitudinal axis of a given one-dimensional image with the correspondingly positioned image segments in all of the other one-dimensional images to produce a projected value for each image segment position; and means for analyzing said projected values to determine whether or not said projected values include a predetermined value that would result if said object plane for said product included said straight line segment.

24. The apparatus defined in claim 23 wherein said means for forming a plurality of one-dimensional images comprises:

a Dove prism mounted for rotation about a rotational axis perpendicular to said object plane for producing an image of said object plane which is rotated by an amount determined by the angle of rotation of said Dove prism about said rotational axis;

means for focusing said rotated image to a one-dimensional image line; and means for rotating said Dove prism through a predetermined rotational angle to cause said plurality of one-dimensional images to form one after another in succession at said one-dimensional image line.

25. The apparatus defined in claim 24 wherein said means for integrating comprises:

a plurality of photodetectors disposed at said one-dimensional image line, each photodetector detecting an image segment having a respective one of said image segment positions.

26. The apparatus defined in claim 25 wherein said means for integrating further comprises:

means for causing each photodetector to integrate the image segment it receives during rotation of said Dove prism through said predetermined rotational angle.

27. Apparatus for determining whether or not a product has predetermined optically detectable properties including two parallel, optically detectable straight line segments in a predetermined object plane, said straight line segments being spaced from one another by a predetermined perpendicular distance, comprising:

means for forming a plurality of one-dimensional images of said object plane for said product, each one-dimensional image having a different angle of orientation parallel to said object plane, and each one-dimensional image including a plurality of image segments spaced along the longitudinal axis of said one-dimensional image;

means for separately integrating the image segment at each position along the longitudinal axis of a given one-dimensional image with the correspondingly positioned image segments in all of the other one-dimensional images to produce a projected value for each image segment position; and means for analyzing said projected values to determine whether or not said projected values include two predetermined values separated by a predetermined image segment position difference that would result if said object plane for said product included said two straight line segments.

28. Apparatus for determining whether or not an object plane of a product has predetermined optically detectable properties comprising:

means for detecting the image intensity of a plurality of points in said object plane to produce image intensity data regarding said object plane;

Hough transform means for transforming said image intensity data to Hough array data such that optically detectable straight line segments having a plurality of nonparallel orientations in said object plane are transformed to points in said Hough array data, each possible straight line segment in said object plane being represented in said Hough array data by first, second, and third Hough array coordinates, said first coordinate being representative of the distance of said straight line segment from an origin point in said object plane, said second coordinate being representative of the angle of inclination of said straight line segment in said object plane, and said third coordinate being representative of the amount of optical information in said straight line segment; and means for analyzing said Hough array data to determine whether or not said Hough array data includes at least one point that would result in said Hough array data if said object plane included said predetermined optically detectable properties, said means for analyzing comprising:

means for projecting said Hough array data parallel to one of said first and second coordinates to produce projected Hough array data; and means for analyzing said projected Hough array data to determine whether or not said projected Hough array data includes at least one point that would result in said projected Hough array data if said object plane included said predetermined optically detectable properties.

29. The apparatus defined in claim 28 wherein said Hough transform means comprises:

computer generated holograms means.

30. Apparatus for determining whether or not an object plane of a product has predetermined optically detectable properties comprising:

means for detecting the image intensity of a plurality of points in said object plane to produce image intensity data regarding said object plane;

Hough transform means for transforming said image intensity data to Hough array data such that optically detectable straight line segments in said object plane are transformed to points in said Hough array data, each possible straight line segment in said object plane being represented in said Hough array data by first, second, and third Hough array coordinates, said first coordinate being representative of the distance of said straight line segment from an origin point in said object plane, said second coordinate being representative of the angle of inclination of said straight line segment in said object plane, and said third coordinate being representative of the amount of optical information in said straight line segment; and means for analyzing said Hough array data to determine whether or not said Hough array data includes at least one point that would result in said Hough array data if said object plane included said predetermined optically detectable properties, wherein said object plane has at least one degree of freedom with respect to its positioning relative to said means for detecting, and wherein said means for analyzing comprises:

means for comparing selected portions of said Hough array data to corresponding data for a product which is properly positioned relative to said means for detecting; and means responsive to said means for comparing for correcting said Hough array data to reverse any effect on said Hough array data due to motion of said product as a result of said at least one degree of freedom.

31. The apparatus defined in claim 30 wherein said Hough transform means comprises:

computer generated hologram means.

32. Apparatus for determining whether or not an object plane of a product has predetermined optically detectable properties comprising:

means for detecting the image intensity of a plurality of points in said object plane to produce image intensity data regarding said object plane, said means for detecting including means for rendering said image intensity data in polar coordinate form;

Hough transform means for transforming said image intensity data to Hough array data such that optically detectable straight line segments in said object plane are transformed to points in said Hough array data, said Hough array data having one angular coordinate; and means for analyzing said Hough array data to determine whether or not said Hough array data includes at least one point that would result in said Hough array data if said object plane included said predetermined optically detectable properties;

wherein said Hough transform means comprises:

a plurality of light sources each producing light having intensity proportional to said image intensity data at a respective one of a plurality of radius values in said polar coordinate form image intensity data;

a plurality of acousto-optic deflector means;

means for directing light from each of said light sources to a respective one of said acousto-optic deflector means;

means for applying a signal which is a sinusoidal function of said angular coordinate to each of said acousto-optic deflector means;

a plurality of photodetectors; and means for focusing light from all of said acousto-optic deflector means to said photodetectors.

33. Apparatus for determining whether or not an object plane of a product has predetermined optically detectable properties comprising:

means for detecting the image intensity of a plurality of points in said object plane to produce image intensity data regarding said object plane;

Hough transform means for transforming said image intensity data to Hough array data such that optically detectable straight line segments in said object plane are transformed to points in said Hough array data; and means for analyzing said Hough array data to determine whether or not said Hough array data includes at least one point that would result in said Hough array data if said object plane included said predetermined optically detectable properties;

wherein said object plane has at least one degree of freedom with respect to its positioning relative to said means for detecting, and wherein said means for analyzing comprises:

means for processing said Hough array data to determine the amount by which said Hough array data is shifted relative to the corresponding data for a product which does not have said at least one degree of freedom;

wherein said means for processing comprises:

a plurality of light sources each of which produced light having intensity proportional to a respective one of a plurality of samples of said Hough array data;

acousto-optic deflector means;

means for applying light from said light sources to said acousto-optic deflector means;

means for applying to said acousto-optic deflector means a signal serially representative of said plurality of samples of said corresponding data;

photodetector means;

means for directing light from said acousto-optic deflector means to said photodetector means; and means for detecting a maximum in said photodetector means output to indicate a correlation between said samples of said Hough array data and said samples of said corresponding data.

34. The apparatus defined in claim 33 wherein said Hough transform means comprises:

computer generated hologram means.

* * * * *

UNITED STATES PATENT AND TRADEMARK OFFICE
CERTIFICATE OF CORRECTION

PATENT NO. : 4,906,099

DATED : March 6, 1990

INVENTOR(S) : David P. Casasent

It is certified that error appears in the above-identified patent and that said Letters Patent is hereby corrected as shown below:

| Column | Line | Correction |
|---|---|---|
| 28 | 34 | Change "sourced" to --sources--. |
| 32 | 45 | Change "produced" to --produces--. |

Signed and Sealed this

Fourteenth Day of January, 1992

*Attest:*

HARRY F. MANBECK, JR.

*Attesting Officer*

*Commissioner of Patents and Trademarks*